(12) United States Patent
Fan

(10) Patent No.: US 11,464,975 B2
(45) Date of Patent: Oct. 11, 2022

(54) METHODS AND APPARATUSES FOR CONFIGURING ARTIFICIAL RETINA DEVICES

(71) Applicant: IRIDIUM MEDICAL TECHNOLOGY CO., LTD., Hsinchu (TW)

(72) Inventor: Long-Sheng Fan, Hsinchu (TW)

(73) Assignee: IRIDIUM MEDICAL TECHNOLOGY CO., LTD., Hsinchu (TW)

(*) Notice: Subject to any disclaimer, the term of this patent is extended or adjusted under 35 U.S.C. 154(b) by 217 days.

(21) Appl. No.: 16/556,634

(22) Filed: Aug. 30, 2019

(65) Prior Publication Data

US 2019/0388688 A1 Dec. 26, 2019

Related U.S. Application Data

(60) Continuation-in-part of application No. 15/642,097, filed on Jul. 5, 2017, now abandoned, which is a division of application No. 14/320,398, filed on Jun. 30, 2014, now Pat. No. 9,737,710.

(51) Int. Cl.
| | |
|---|---|
| *A61N 1/36* | (2006.01) |
| *A61N 1/372* | (2006.01) |
| *A61N 1/05* | (2006.01) |
| *H01L 23/498* | (2006.01) |

(52) U.S. Cl.
CPC ....... *A61N 1/36046* (2013.01); *A61N 1/0543* (2013.01); *A61N 1/37223* (2013.01); *H01L 23/4985* (2013.01); *H01L 2924/0002* (2013.01)

(58) Field of Classification Search
CPC ............ A61N 1/37223; A61N 1/36046; A61N 1/0543
See application file for complete search history.

(56) References Cited

U.S. PATENT DOCUMENTS

| | | | |
|---|---|---|---|
| 5,755,748 A | 5/1998 | Borza | |
| 9,302,103 B1* | 4/2016 | Nirenberg | .......... A61N 1/36003 |
| 2012/0109295 A1 | 5/2012 | Fan | |
| 2012/0109296 A1* | 5/2012 | Fan | ...................... A61N 1/0543 623/6.63 |

* cited by examiner

*Primary Examiner* — Alyssa M Alter
(74) *Attorney, Agent, or Firm* — Muncy, Geissler, Olds & Lowe, P.C.

(57) ABSTRACT

Methods and apparatuses to detect configuration commands from waveforms received at a retina prosthesis device for calibrating the device are described. The device can comprise an array of pixel units to receive light to stimulate neuron cells to cause an effect of visual sensation from the light. The pixel units may have configurable parameters for the stimulation to the neuron cells. The configurable parameters may be updated according to the configuration commands detected without requiring micro processor and non-volatile memory in the device. The stimulation may be generated according to the updated configurable parameters to improve the effect of visual sensation from the light including compensation for the physiological and environmental variations and drifts.

1 Claim, 28 Drawing Sheets

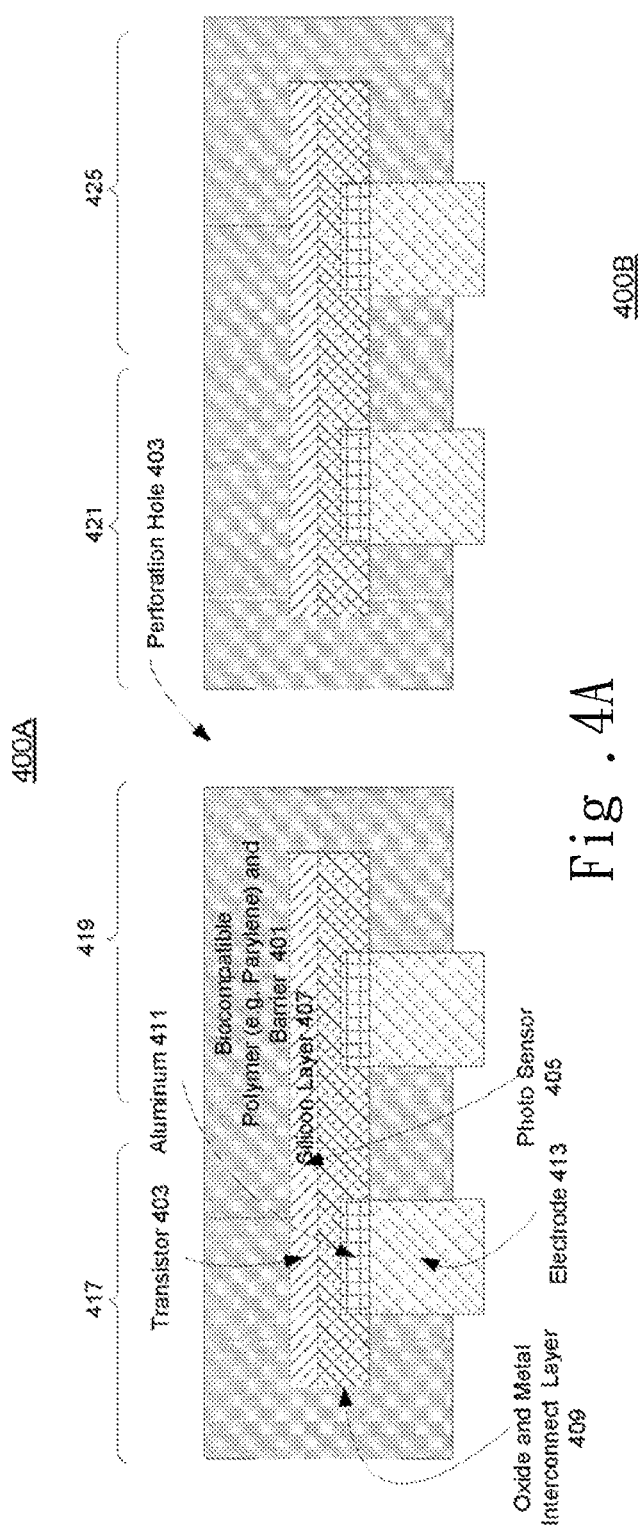
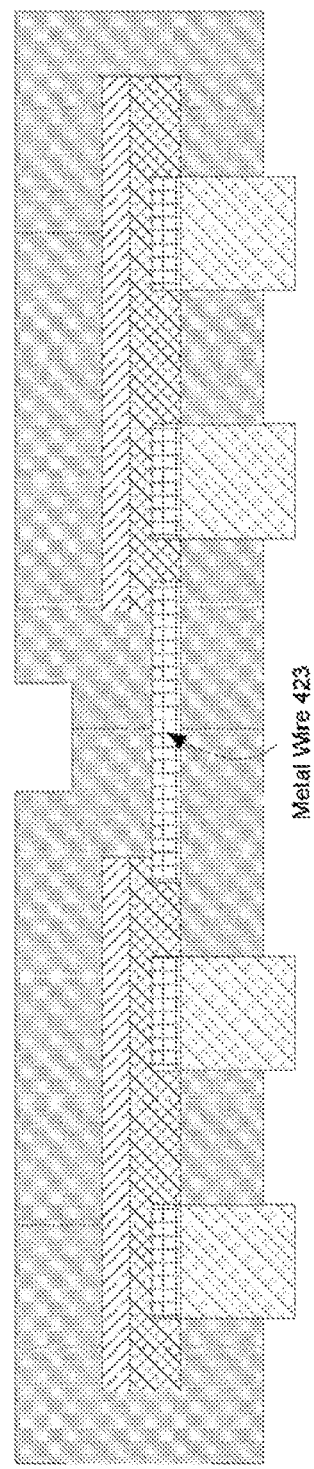
Fig. 4A
Fig. 4B

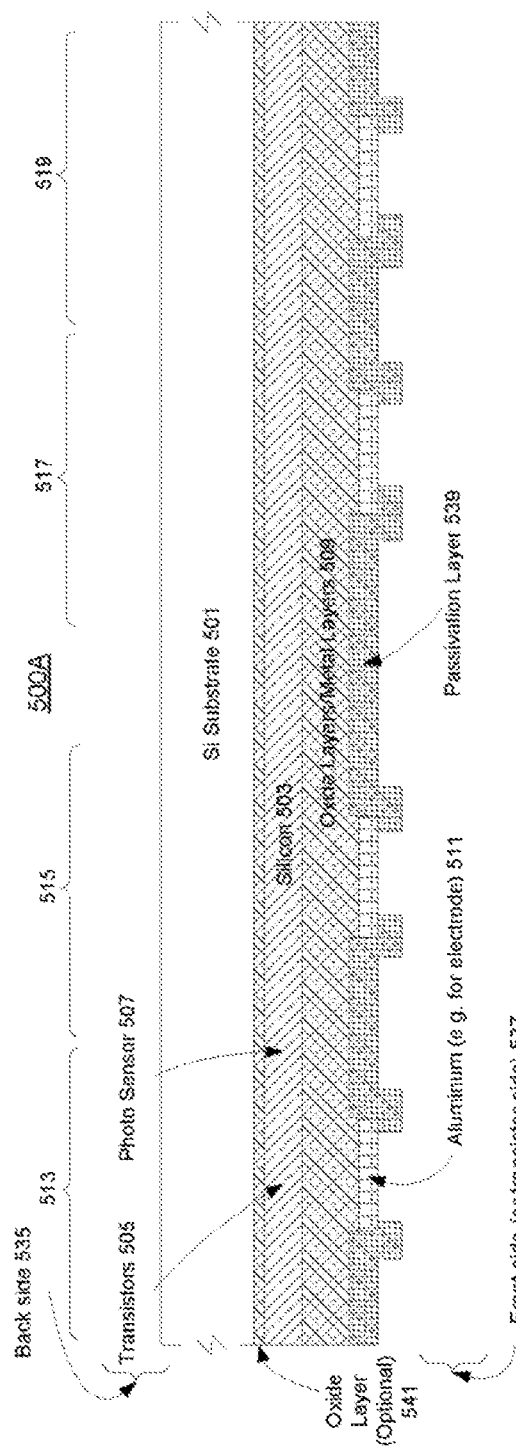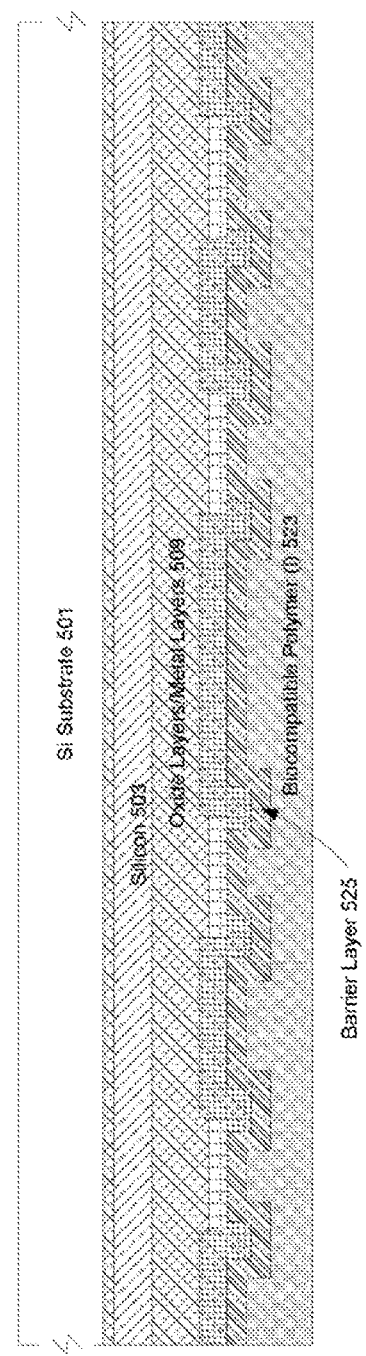
Fig. 5A
Fig. 5B

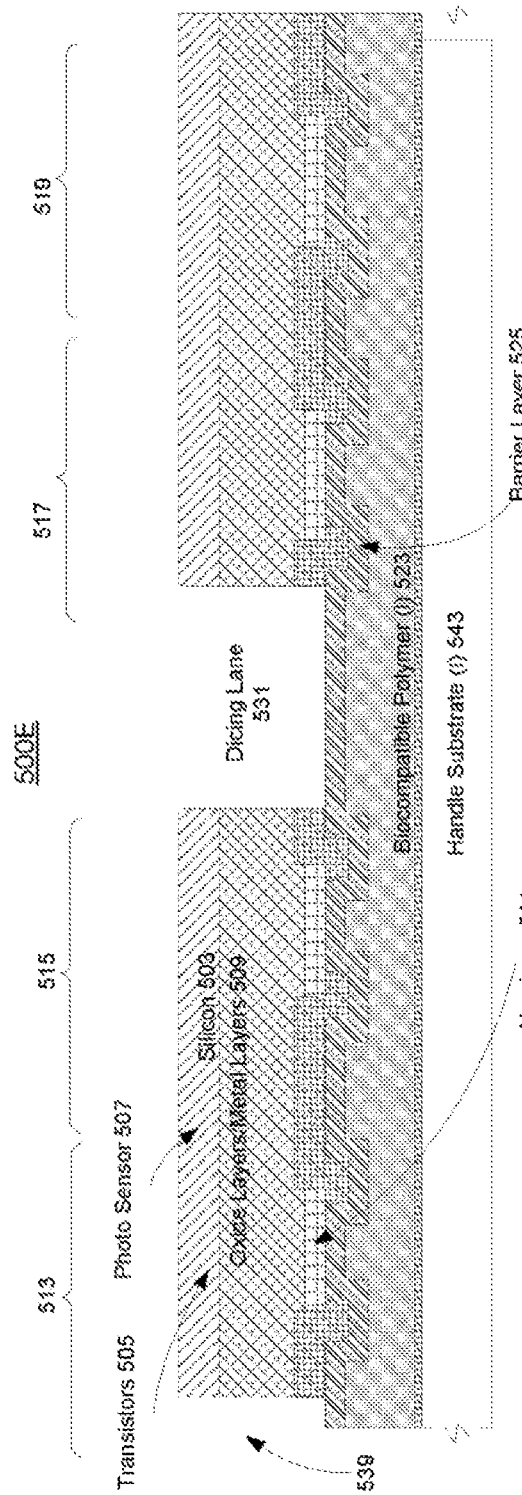
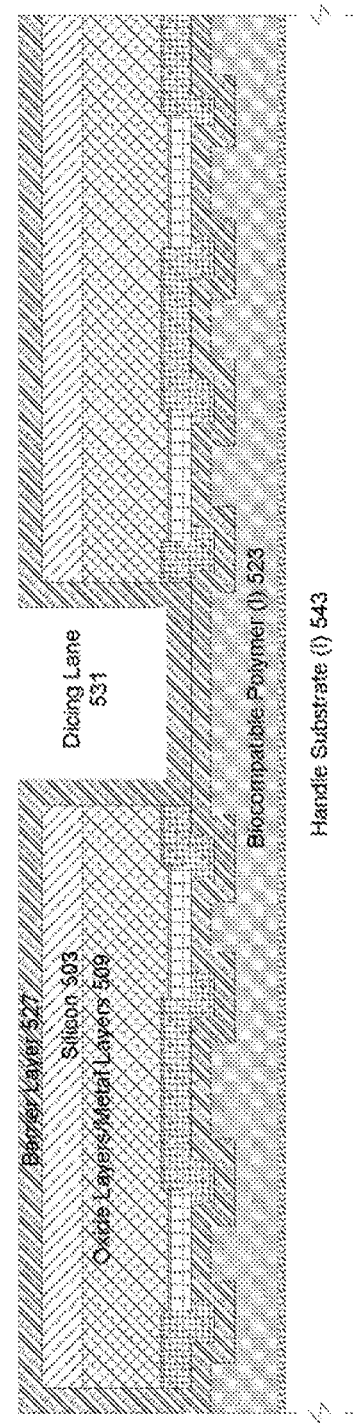
Fig. 5E
Fig. 5F

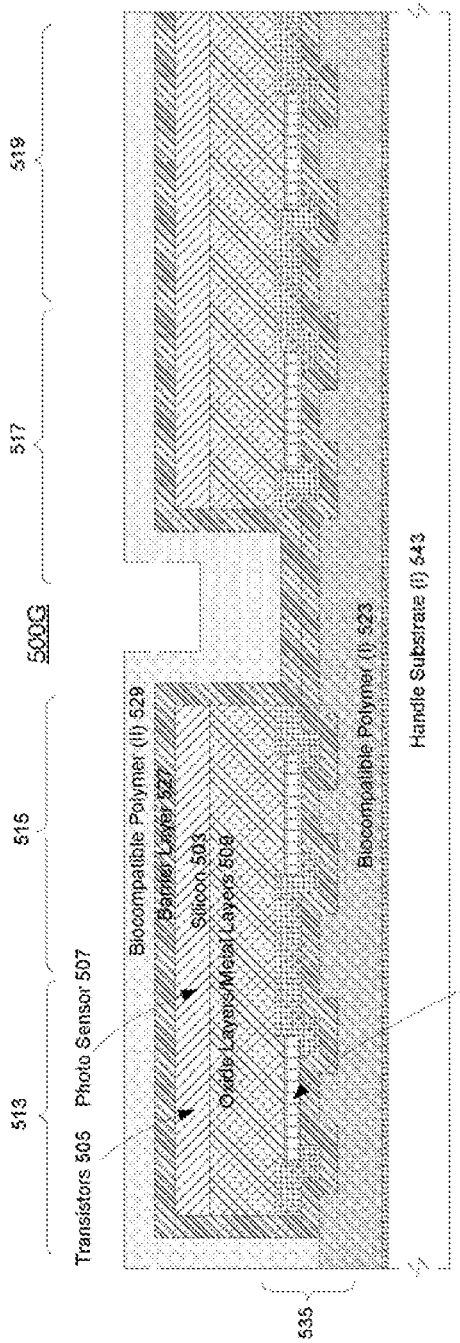
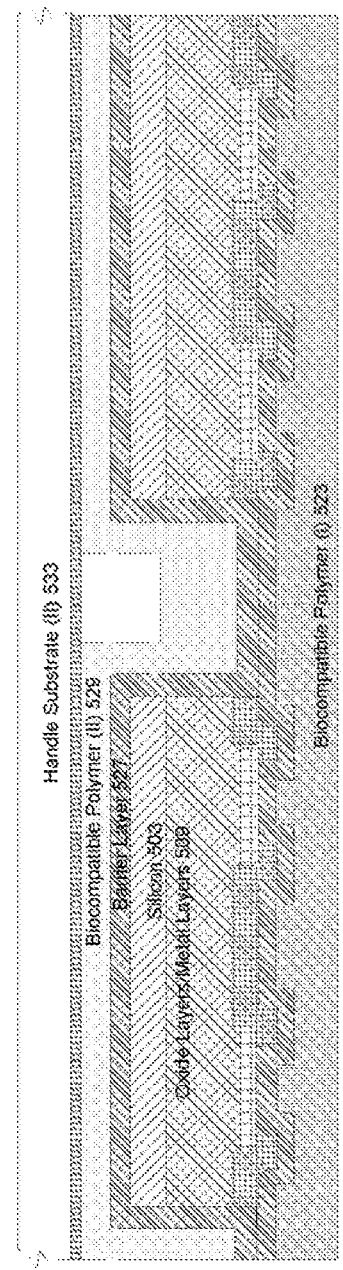

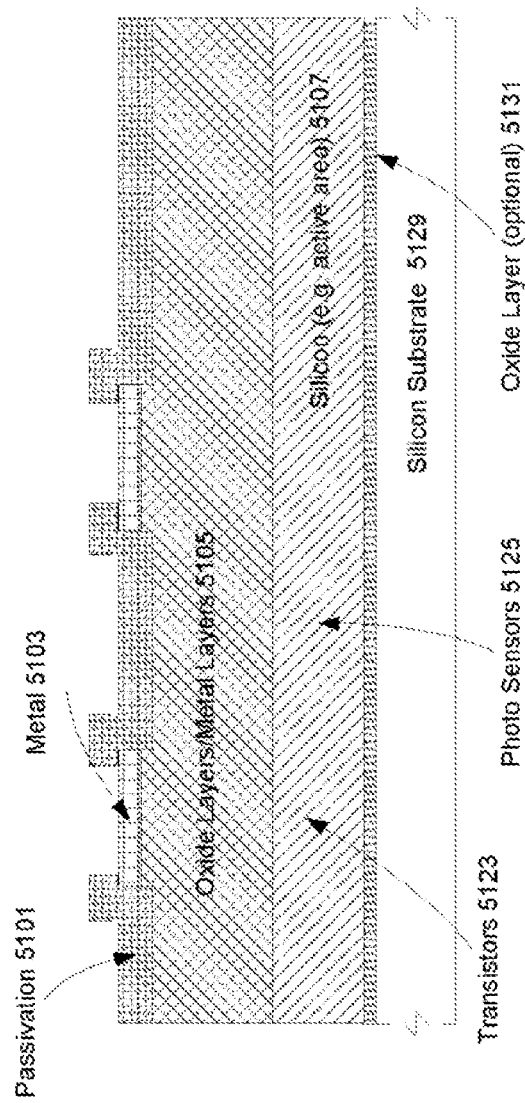
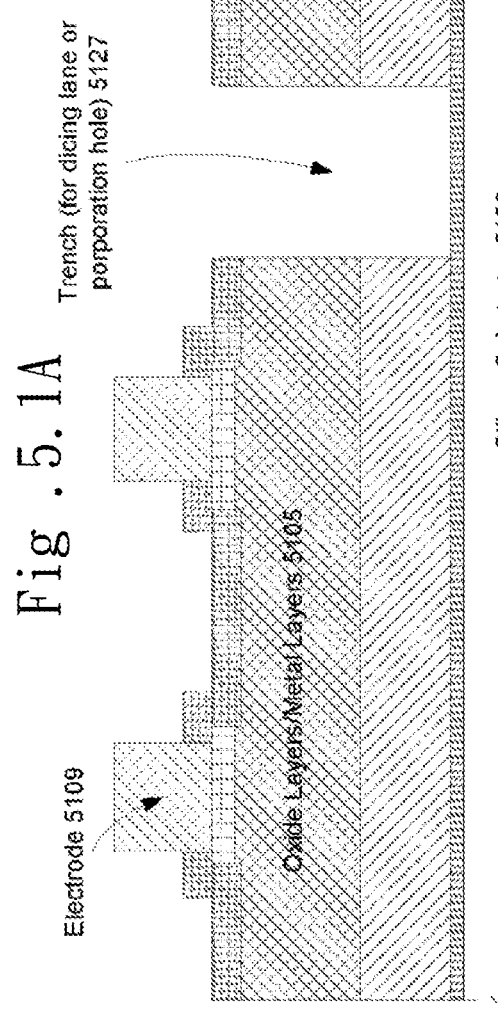
Fig. 5.1A
Fig. 5.1B

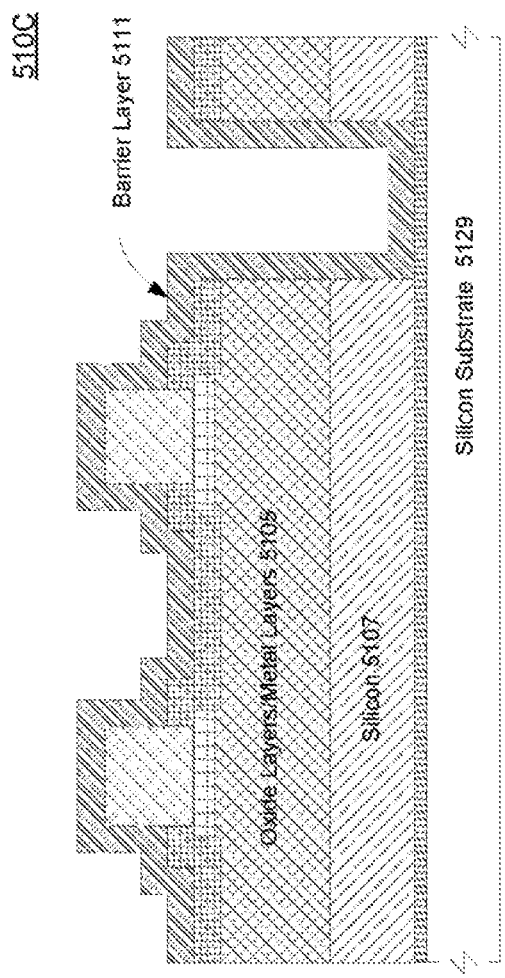
Fig. 5.1C
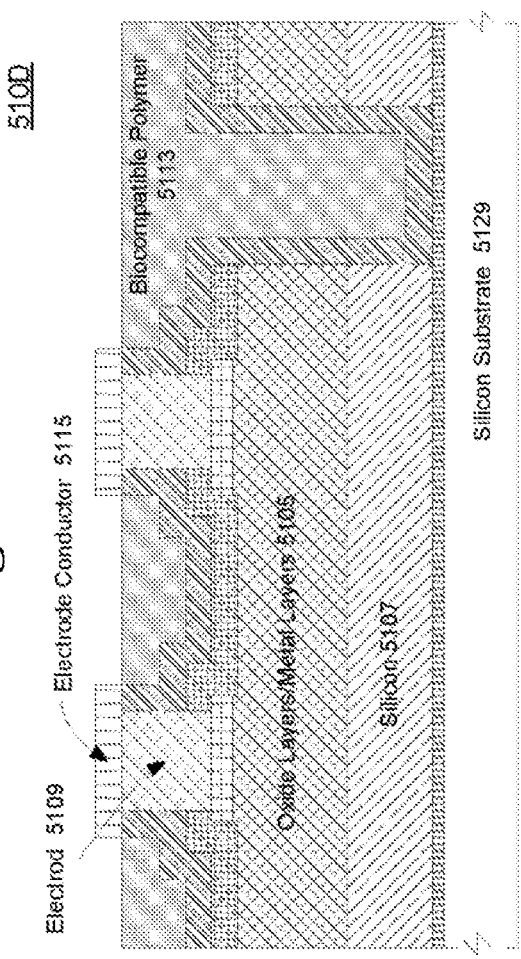
Fig. 5.1D

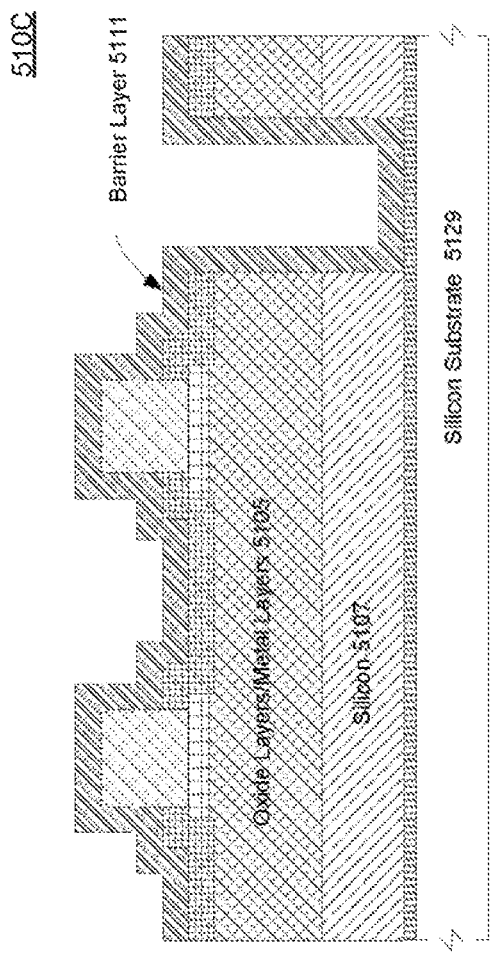
Fig. 5.1E
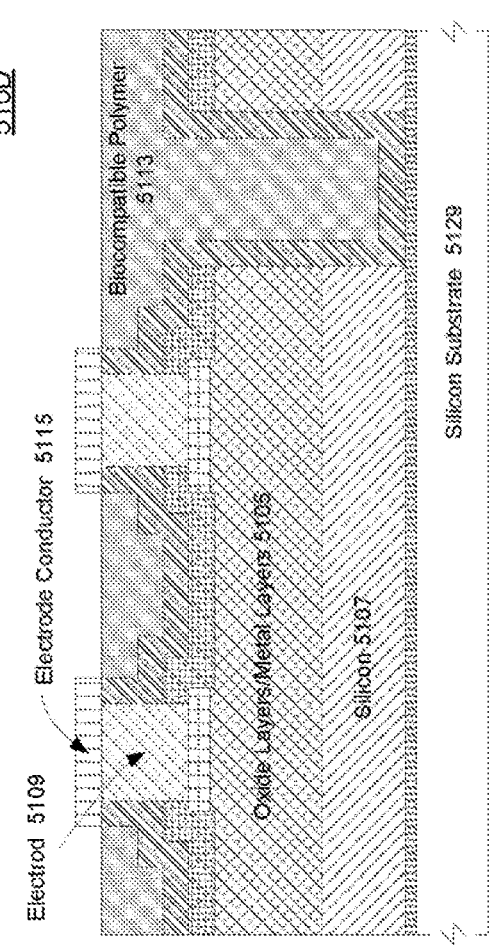
Fig. 5.1F

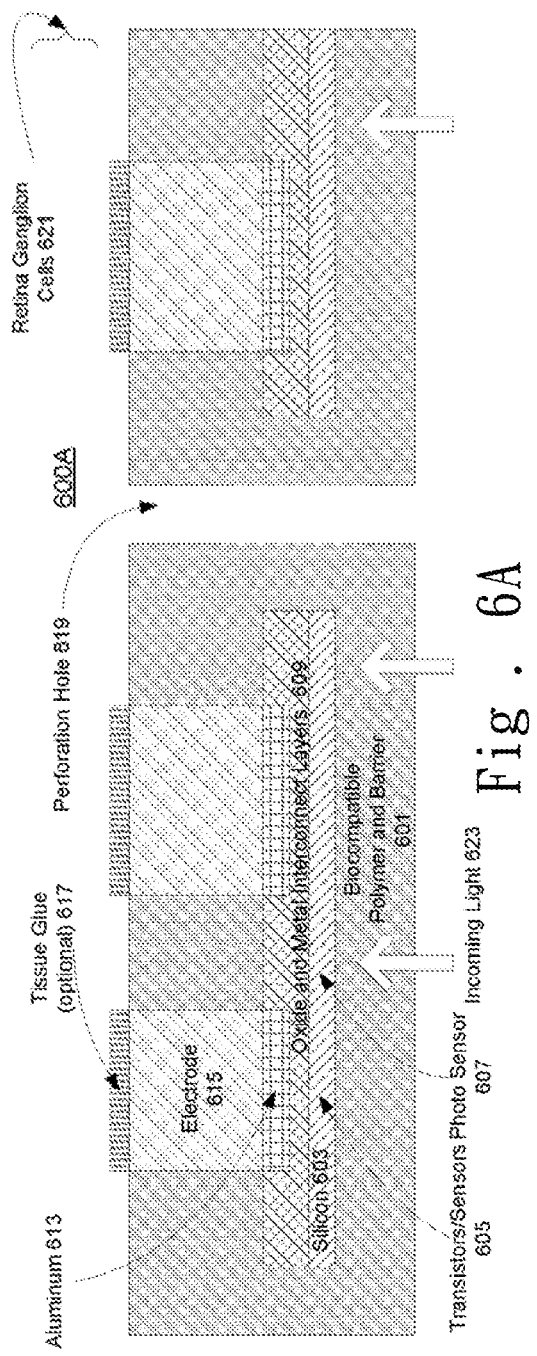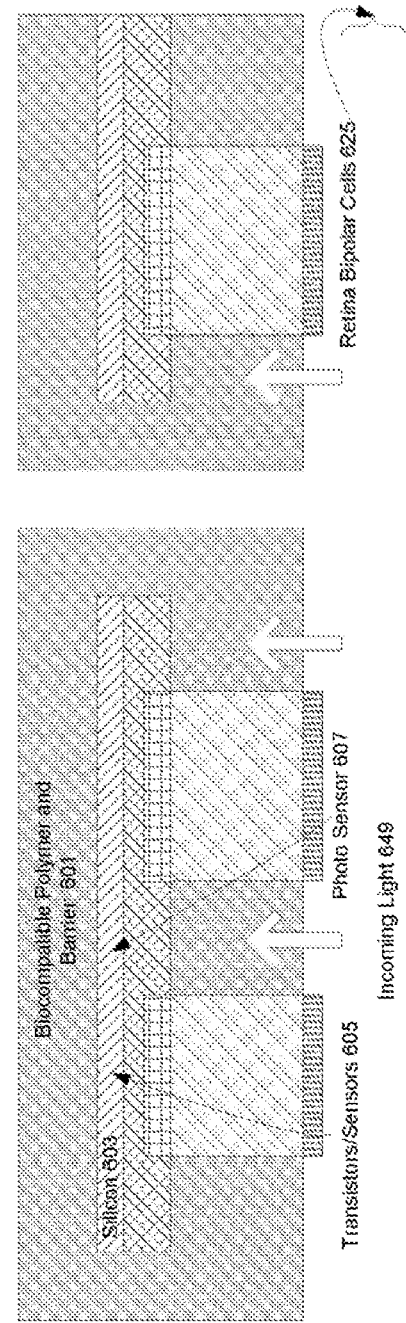
Fig. 6A
Fig. 6B

1300

Detecting predetermined light patterns to cause a device into a calibration mode, wherein the device comprises an array of pixel units to receive light to enable perception of vision of the light, and wherein the pixel units are configurable via electrical parameters 1301

Receiving light patterns to select one or more pixel units from the array, the light patterns associated with known effect of visual sensation 1303

Generating stimuli from the selected pixel units to stimulate neuron cells to cause actual effect of visual sensation via the light patterns 1305

In response to receiving external commands, updating the electrical parameters for the selected pixel units to improve the actual effect of visual sensation for the known effect of visual sensation 1307

```
Receiving test commands from an interface at a device, the device comprising an
array of pixel units to receive light to stimulate neuron cells to cause an effect of
visual sensation from the light, the pixel units having configurable parameters for
the stimulation to the neuron cells 1601
                                    │
                                    ▼
Sending data related to electric characteristics of the neuron cells via the interface
                        according to the test commands 1603
                                    │
                                    ▼
       Detecting configuration commands received at the interface subsequent to
                            sending the data 1605
                                    │
                                    ▼
       Updating the configurable parameters according to the configuration commands
                                detected 1607
                                    │
                                    ▼
       Generating the stimulation according to the updated configurable parameters to
              improve the effect of visual sensation from the light 1609
```

Fig . 17

METHODS AND APPARATUSES FOR CONFIGURING ARTIFICIAL RETINA DEVICES

CROSS REFERENCE TO RELATED APPLICATIONS

This application is a continuation-in-part application of U.S. patent application Ser. No. 15/642,097, filed on Jul. 5, 2017, which is a divisional application of U.S. patent application Ser. No. 14/320,398, filed Jun. 30, 2014. The disclosure of the above applications is incorporated by reference herein in their entirety.

FIELD OF THE INVENTION

The present invention relates generally to micro devices, and more particularly to flexible integrated circuit devices capable of stimulating neural cells.

BACKGROUND OF THE INVENTION

Age-related macular disease (AMD) and the retinitis pigmentosa (RP) disease have been identified as major causes of blindness, especially for senior people worldwide. Retinal prosthesis device offers possible restoration of part of the vision to the blindness. Typically, the device includes electrodes requiring separate wiring implant to control each electrode. However, field of view provided by such devices, which depends on the number of electrodes included in the device, may be severely limited because of size limitation on the wiring implant.

Furthermore, the image resolution of a retina prosthesis device may be related to density of electrodes in the device. Conventional devices for retina prosthesis may include driving circuit chips separate from electrode or image sensor chips implanted to retina tissues. Thus, the required number of electrical interconnections between the electrode chips and the driving circuit chips can increase significantly to impose unnecessary ceilings on possible image resolution achievable.

In addition, existing retina prosthesis devices may be based on electrodes made of planner chips not conforming to non-planar shapes of retina tissues. As a result, additional interferences among the electrodes may occur because of the mismatch in shapes to further limit possible image resolution of the device.

Thus, traditional retina prosthesis devices are inherently limited to provide levels of image resolutions, field of views or other visual characteristics to achieve levels close to a real retina to help patients recover from impaired vision capabilities.

SUMMARY OF THE INVENTION

In one embodiment, a flexible integrated device can provide high resolution of electrical excitations (e.g. down to individual retina cell level) over at least one mm (million meter) to several mm field of view for retina prosthesis. The flexible integrated device may be capable of tuning and calibration for adjusting excitation to target retinal neurons. In one embodiment, the flexible integrated device may be implanted using either an epi-retinal (e.g. from the front side of retina or on the retina) approach or a sub-retinal (e.g. behind the retina) approach.

In another embodiment, a single flexible CMOS (complementary metal-oxide-semiconductor) chip can integrate an array of pixel units. Each pixel may comprise an electrode, photo sensor, signal processor and driver circuitry. The flexible chip can be fabricated thin enough to conform to the shape of a retina. For example, the flexible chip about 3 mm in diameter may be bendable to about 90 µm (micro meter) along the edge of the chip to form a two dimensional curved spherical device.

In another embodiment, a flexible integrated device may include a mosaic of sub-modules divided via boundaries. Device material except some conducting lines (e.g. metal lines) between these sub-modules may be removed from the boundaries to increase moldability (e.g. flexibility to conform to different shapes) of the device. In some embodiments, the flexible integrated device may be perforated (e.g. with perforation holes) to maintain some fluidic flow across the device. Optionally or alternatively, the flexible integrated device may include a thin substrate to allow a portion of light (e.g. when not obstructed by metals) to penetrate through the chip to be applicable in epi-retinal prosthesis.

In another embodiment, a flexible integrated device may include electrodes fitted with local return paths (or "guard ring") to shorten the total distance of electric flows from the electrodes. As a result, the amount of electricity lost in transit of the electric flows can be lowered to prevent unwanted stimulation of sensory cells other than target neuron cells, such as the bipolar cells and ganglion cells situated behind the retina. The electrodes may be positioned in three dimensions with multiple electrode heights from surfaces of the device to differentially stimulate different types of neuron cells, such as strata of ON and OFF cells.

In another embodiment, a flexible integrated device may include on-chip signal processing circuitry capable of generating appropriate stimulus waveforms for a pixel unit by taking inputs from multiple pixel units, such as nearby neighboring pixel units. The flexible integrated device may include electrical sensing circuitry capable of identifying specific types of target neural cells for each pixel unit through receptive field and firing patterns from the target neural cells (e.g. located close to the pixel unit).

In another embodiment, a provision system including a flexible integrated retina chip implanted to a user as retina prosthesis may allow fine tuning of the chip via external commands. For example, each pixel unit in the chip may include specific receivers and/or circuitry for receiving optical and/or wireless communication signals for the external commands to select and/or configure portions of the chip according to the user's visual perception. The provision system may include a remote control to issue the external commands optically or wirelessly.

In another embodiment, an implantable device to interface with retina cells may comprise an array of pixel units capable of stimulating the retina cells. The pixel units may operate in a mode of operation selected from a plurality of modes including a normal mode and a calibration mode. A control circuitry of the device may be configured to switch the mode of operation for the pixel units. In one embodiment, the pixel units may be configured to receive light for stimulating the retina cells during the normal mode to enable perception of the images of the lights. During the calibration mode, the pixel units may be configured to adjust amount of stimulation (strength or amplitude, duration, duty cycle, repetition rate of a waveform, or spike sequences representing the stimulation etc.) to the retina cells.

In another embodiment, a method to calibrate a retina prosthesis device may comprise detecting predetermined pre-amble of light patterns (in space and time) or RF signal sequence to cause the device into a calibration mode. The device may comprise an array of pixel units to receive light to enable perception of vision of the images of the lights. The pixel units may be configurable via electrical parameters. Light patterns or RF (Radio Frequency) signal sequence may be received to select one or more pixel units from the array. In one embodiment, the light patterns may be associated with known effect of visual sensation. Stimuli may be generated from the selected pixel units to stimulate neuron cells to cause actual effect of visual sensation via the light patterns captured by the selected pixel units. In response to receiving external commands, the electrical parameters may be updated for the selected pixel units to improve the actual effect of visual sensation for the known effect of visual sensation.

In another embodiment, a system for retina prosthesis calibration may comprise a retina prosthesis device to interface with retina cells and a remote control device capable of sending external commands to the device. The device may include a plurality of photo sensors to receive light, a plurality of electrodes to stimulate the retina cells, a configurable processing circuitry to generate stimuli for the electrodes based on the light received, and control circuitry to configure the configurable processing circuitry according to the external commands. A known visual perception may be projected via the light. In one embodiment, the external commands may be capable of selecting one or more of the photo sensors and the electrodes. Optionally or alternatively, the external commands may be capable of selecting a configuration of the configurable processing circuitry via a comparison between an actual perception of vision from the stimulated neuron cells and the known perception of vision. The configurable processing circuitry may generate the stimuli according to the configuration.

In another embodiment, configuration commands can be detected from waveforms received at a retina prosthesis device for calibration. The device can comprise an array of pixel units to receive light to stimulate neuron cells to cause an effect of visual sensation from the light. The pixel units may have configurable parameters for the stimulation to the neuron cells. The configurable parameters may be updated according to the configuration commands which are detected without requiring processor logic (e.g. a micro processor and/or associated memory components) in the device. The stimulation may be generated according to the updated configurable parameters to improve the effect of visual sensation from the light.

Other features of the present invention will be apparent from the accompanying drawings and from the detailed description that follows.

BRIEF DESCRIPTION OF THE DRAWINGS

FIGS. 4A-4B are block diagrams illustrating cross sectional views of flexible devices in one embodiment of the present invention;

FIGS. 5A-5J are block diagrams illustrating a sequence of fabrication processes for flexible devices in one embodiment of the present invention;

FIGS. 5.1A-5.1F are block diagrams illustrating a sequence of fabrication processes for flexible devices in another embodiment of the invention;

FIGS. 6A-6D are block diagrams illustrating exemplary layered structures of flexible devices for different approaches to implant retina prosthesis;

FIG. 14 is a flow diagram illustrating a method to configure flexible devices in one embodiment described herein;

FIG. 17 is a flow diagram illustrating another method to configure flexible devices in one embodiment described herein.

DETAILED DESCRIPTION OF THE PREFERRED EMBODIMENTS

Figure 1A:
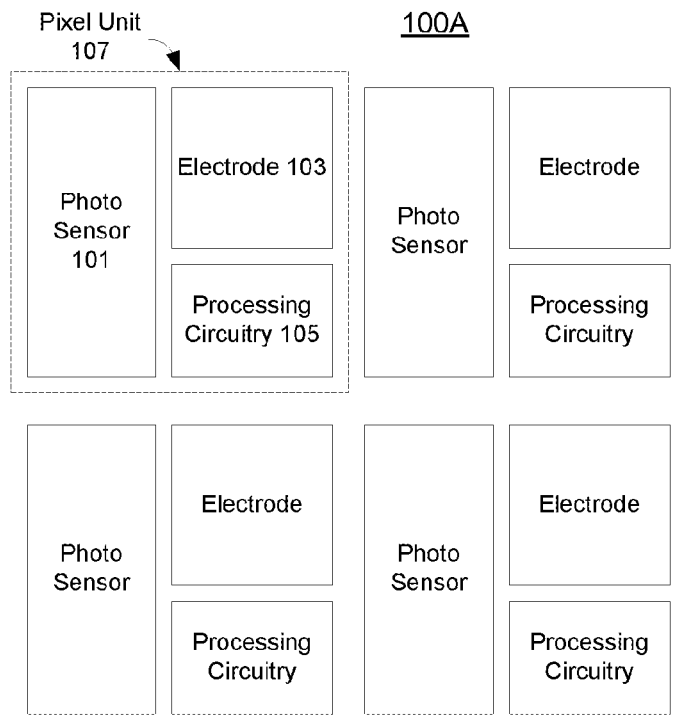
FIGS. 1A-1B are block diagrams illustrating embodiments of integrated flexible devices for retina prosthesis.

Methods and apparatuses for configuring artificial retina devices are described herein. In the following description, numerous specific details are set forth to provide thorough explanation of embodiments of the present invention. It will be apparent, however, to one skilled in the art, that embodiments of the present invention may be practiced without these specific details. In other instances, well-known components, structures, and techniques have not been shown in detail in order not to obscure the understanding of this description.

Reference in the specification to "one embodiment" or "an embodiment" means that a particular feature, structure, or characteristic described in connection with the embodiment can be included in at least one embodiment of the invention. The appearances of the phrase "in one embodiment" in various places in the specification do not necessarily all refer to the same embodiment.

A flexible IC (integrated circuit) device can integrate an array of "pixels" in a sing chip. Each pixel can comprise an electrode, sensors (e.g. photo sensors, electric sensors or other applicable sensors), a signal processor and/or driver circuitry. The integration can simplify wiring, fan out, multiplexing or other requirements to enable intended functions of the device. Costly signal transmission, for example, via EM (electromagnetic) waves, between processing circuitry and sensor/electrode arrays may be eliminated. Each pixel can be accessible within the device to allow thousands or tens of thousands of pixels in the device to interface with neuron cells. For example, the flexible integrated device may provide required density to restore 20/80 vision corresponding to about a two to three mm-sized, high density array with 10,000~20,000 pixel units.

In one embodiment, flexibility of an integrated device may be based on controlled thickness of the device. For example, the device can be thin enough to bend ~90 μm to conform to the shape of a retina (e.g. a human eye ball). In some embodiments, the device may be made (e.g. according to a fabrication process) thin enough to be bent to a radius of curvature smaller than 12 mm, about the average radius curvature of a human retina, still within the safety margin of the material strength of the device.

As a device is bendable to conform to the curvature of a retina, the neuron-to-electrode distance between electrodes of the device and target neuron cells of the retina can be minimized. Consequently, the power required in the device to excite or stimulate the neuron cells can be reduced to enable a higher pixel density and improve resolution of images perceived via the neuron cells using the device implanted to a patient. In certain embodiments, the device can meet the conformity requirements for exciting individual retinal neuron (e.g. targeting an individual neuron cell per electrode).

In one embodiment, a flexible integrated circuit (or device) for retina prosthesis may be fabricated based on an 180 nm (nanometer) CMOS technology using 1~30 micrometer thick Si device layer sandwiched between two biocompatible polymer and barrier layers (such as Polyimide/SiC, Parylene/SiC). Both biocompatible polymer and barrier layer may be compatible (e.g. biocompatible) with ISO (International Organization for Standardization) 10993 standards to provide mutual protection between the flexible integrated device and surrounding tissues when the device is implanted within the tissues. The barrier layer may be denser than the biocompatible layer to strengthen the protection.

The fabrication approach of a flexible integrated device may enable integration of high density CMOS image sensors and signal processing circuitry together with neuron stimulating electrode arrays on the same flexible patch needed for medical implants. In some embodiments, semiconductor substrate may be used in the device to allow inclusion of necessary optical and/or electronic components for sensing optical images and producing electrical stimulus as a function of the sensed optical images.

In an alternative embodiment, a flexible integrated device may be applicable in different manners of retina implantation. For example, the device may be manufactured to be thin enough to allow light to pass through the device. Sensors and electrodes may be positioned in the same side (or surface) or opposing sides of such a translucent device. As a result, the device may be implanted in an epi-retina manner to stimulate retinal ganglion cells (RGC) directly via electrodes of the device without utilizing a retinal neural network before the RGC layer. Alternatively, the device may be implanted in a sub-retinal manner to stimulate the retina from the bipolar cell side via the electrodes, for example, to work together with the remaining neural network formed by a variety of neuron cells, such as bipolar cells, horizontal cells, amacrine cells etc.

In one embodiment, a flexible integrated device may be capable of igniting target neuron cells or nerves according to characteristics of the neuron cells responding to light stimuli. For example, the characteristics may indicate the target neuron cells are ON type cells, OFF type cells or other types of cells. An ON type cell may respond substantially synchronous with onset of light stimuli. An OFF type cell may respond substantially synchronous with offset of the light stimuli. The flexible integrated device may include processing capability to generate stimuli from received light to properly ignite the targeted neuron cells (e.g. as if the neuron cells are directly stimulated by the received light), for example, via special stimulation pattern (or waveforms), time delays, ignition, suppression, or other applicable stimulation manners, etc. In one embodiment, the flexible integrated device may include multiple layers of electrodes (e.g. distributed in a three dimensional manner) to allow physical selection (e.g. based on proximity) of different layers of neuron cells (e.g. due to neuron connection stratification) to communicate (or stimulate).

A flexible integrated device may be configurable to provide customized functionalities for different retina implant needs. For example, manual and/or self (automatic) calibration operations may be applied in vitro (e.g. subsequent to implantation into a patient) to identify types of targeted neuron cells and/or adjusting sensor/electrode array parameters of the device according to actual visual perception of the receiving patient. Processing functions may be activated or programmed (e.g. through programmable circuitry) to provide equivalent signal processing effects, for example, to replace damaged neuron cell networks to improve impaired vision of the receiving patient.

The flexible integrated device or chip may be wirelessly coupled with a nearby wearable device, such as eyeglasses. Availability of two-way wireless communication between the flexible device and the wearable device may allow the flexible device to operate in different modes to increase its effectiveness. For example, the flexible device may enter a test mode (e.g. before implantation) to enable chip probing without a need for additional pad openings to ensure quality of the device. After implantation of the flexible device, diagnostic tests on the device may be conducted wirelessly when the device is operating in the test mode.

In some embodiments, the flexible device may operate in a calibration mode to allow determination of optimum stimulation waveform (e.g. generated via a pixel array of the device) via wireless calibration of electrode to neuron interface characteristics. External computation power may be leveraged to perform operations via sophisticated algorithms for the determination which may not be feasible within the implantable flexible device constrained by both size and power. During the calibration mode, repeated measurements of neural responses may be conducted according to external commands. Electrodes can send stimulating signals and switch to sensing mode to detect the correlated responses that might be smaller than the noise background. Since the neurons responses is correlated to the stimulation, but noise are not, multiple samples of measurement data (e.g. sensed responses) may be wirelessly transmitted externally to allow application of the oversampling techniques (e.g., by repeating this N time and averaging the sum, the signal to noise ratio will increase sqrt(N) time) to enhance weak/noisy neural responses to more accurately identify load characteristics for determining the optimum stimuli waveforms.

When the flexible device operates in a usage mode or operating mode, configuration parameters (e.g. for pixel unit array) for stimulation waveforms may be received (e.g. wirelessly) at power on. When the flexible device operates in a test or diagnostic mode, test or electrical parameters (e.g. impedance, injection current, voltage to reference electrode etc. of each electrode) of each pixel unit or selected pixel unit(s) may be accessed and sent out (e.g. wirelessly) to external devices.

In some embodiments, when the flexible device is switched to neuron identification mode, test or diagnostic commands may be received to apply testing stimuli to determine interface neuron characteristics. For example, electrodes may by using the oversampling technique as described above to electrically stimulate the neurons (repeated several times) and send sensed signals to external components or devices for processing. As a result, the types of neuron cells interfaced to each electrode can be identified. In certain embodiments, the flexible device may operate in an external assist mode to wirelessly receive parameters (e.g. for generating stimuli) continuously from an external camera or glasses which processes incoming images via processing operations requiring significant processing resources (e.g. using sophisticated algorithms to supplement any lost retinal neural network functions to the implanted chip, identify potential hazardous hindrance objects and send signal to the implanted chip to highlight the objects, or zonal gain controls to the implanted chip for high dynamic range scenes).

Figure 1B:
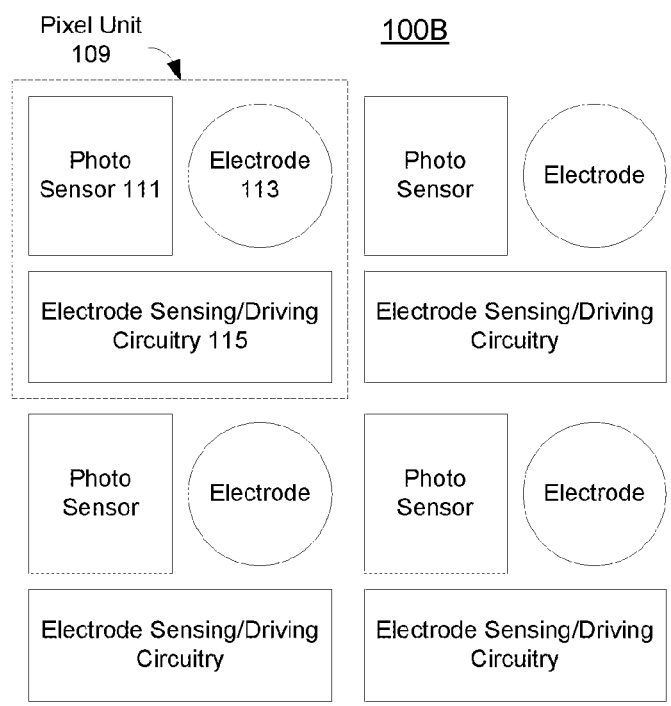

FIGS. 1A-1B are block diagrams illustrating embodiments of integrated flexible devices for retina prosthesis. Device 100A of FIG. 1 may include a two dimensional array of pixel units. Each pixel unit may include similar structures. For example, pixel unit 107 may comprise a photo sensor 101 to receive incoming light, processing circuitry 105 to perform operations, and electrode 103 to stimulate target neuron cells to allow perception of vision projected by the incoming light. In one embodiment, processing circuitry 105 may include digital, analog or other applicable circuits to process sensed light from photo sensor 101 for generating a stimulus or waveform, activation patterns, etc. to drive electrode 103 to stimulate the targeted neuron cells.

Alternatively, device 100B of FIG. 1B may include pixel unit 109 comprising photo sensors 111, electrode 113 and circuitry 115. Electrode 113 may interface with target neuron cells to deliver stimulus to and/or sense electric activities from targeted neuron cells. The stimulus may be derived from light captured by photo sensor 111. In one embodiment, circuitry 115 may provide processing (e.g. signal processing) functions for receiving, processing, and/or driving electric signals. For example, electric signals may be received via sensed light from photo sensor 111 or sensed electrical fields from electrode 113. Circuitry 115 may drive stimulus as electric signals via electrode 113.

The incorporation of electrical sensing circuit 115 in the retinal prosthesis chip device 100B may enable automatic type identification of neuron cells through sensed receptive field (e.g. electrical field) and neuron spiking patterns in time domain. Examples may be functional asymmetries in ON and OFF ganglion cells of primate retina that receptive fields of ON cells is 20% larger than those of OFF cells, resulting in higher full-field sensitivity, and that On cells have ~20% faster response kinetics than OFF cells. A large array of cell-sized micro electrodes conforming to the retina and capable of both sensing and stimulating may allow selective stimulating or suppress ON and OFF retina retinal ganglion cells.

Figure 2A:
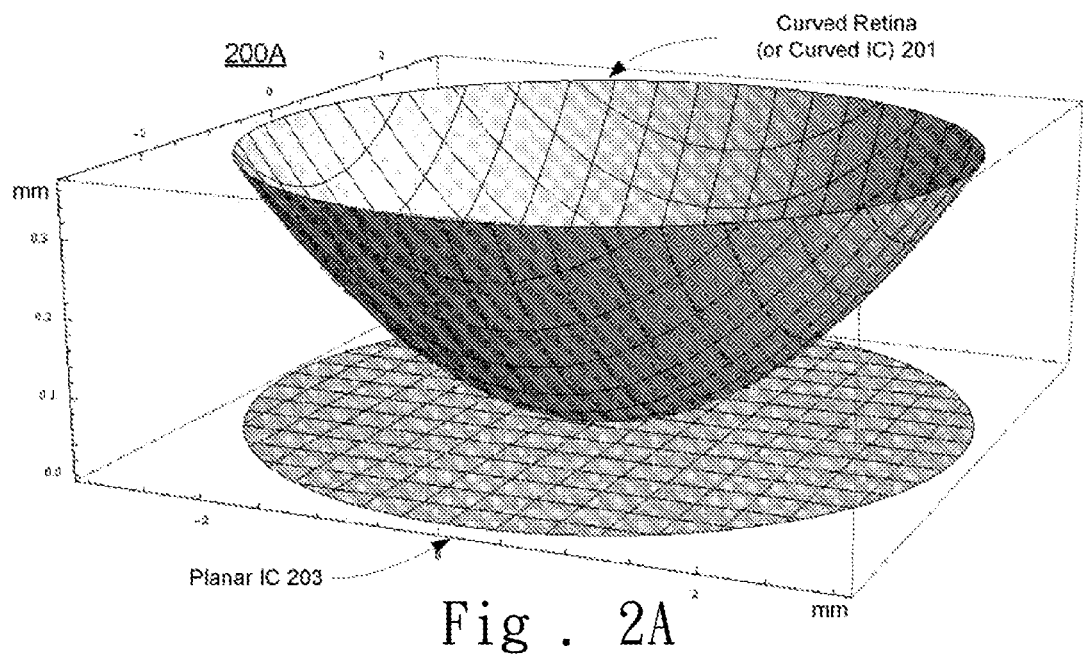
FIGS. 2A-2B are relationship diagrams illustrating effects of flexible devices which are curved according to one embodiment of the present invention.
Figure 2B:
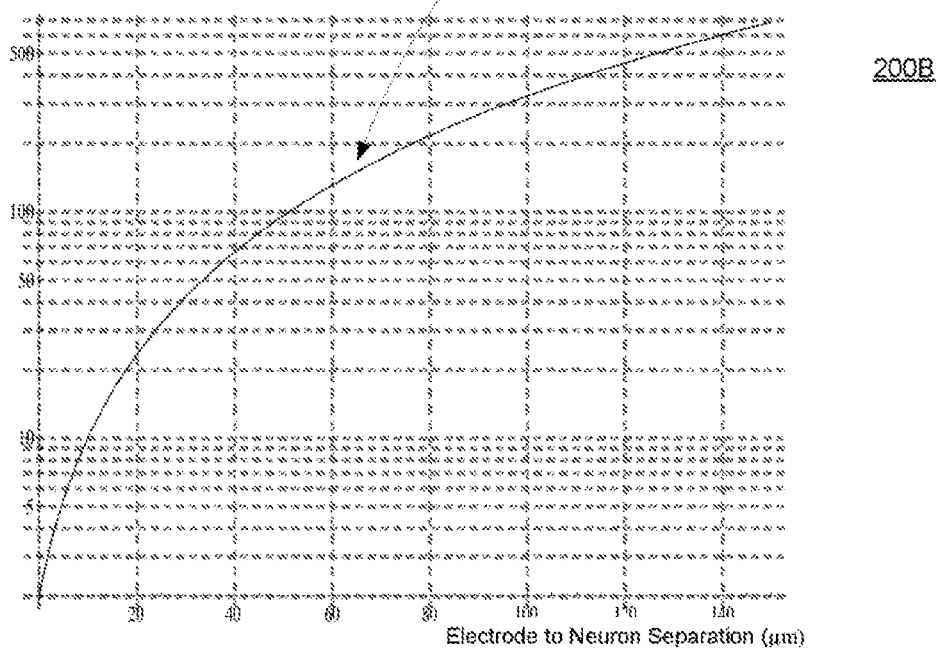

FIGS. 2A-2B are relationship diagrams illustrating effects of flexible devices which are curved according to one embodiment of the present invention. Typically, image resolution and required driving power (e.g. threshold current density) of a retina prosthesis device may depend on curvature of the device. In one embodiment, a flexible integrated device for retina prosthesis may include cell-pitched electrode array (e.g. each electrode is about the size of a single neuron cell) fabricated by planar IC lithography technology. FIG. 2A shows distribution diagram 200A of neuron-to-electrode distances for implementing an mm-sized planner electrode array chip in contact with a retina curved according to a human eye ball, which is roughly spherical with an average diameter of 25 mm.

As shown in distribution diagram 200A, an mm-sized planar electrode array chip 203 in contact with the retina 201 at the chip center may quickly separate from the retina by about 90 microns at distance 1.5 mm from the center toward the edge of the chip. This increase of neuron-to-electrode distance can imply, for example, increase in the threshold current needed for an electrode to depolarize target neurons. As shown in relationship diagram 200B of FIG. 2B, the increase in the threshold current required can be 1~2 orders in magnitude according to curve 205. Additionally, the increase of neuron-to-electrode distance may reduce the resolution to depolarize particular neurons since the field lines and electrical currents (e.g. for sending stimulus signals) from the electrodes may spread out with distance and cover a large area to reach distant neurons. In one embodiment, a flexible integrated device of the present invention may be implanted without the distance or separate implications shown in FIGS. 2A and 2B.

Figure 3:
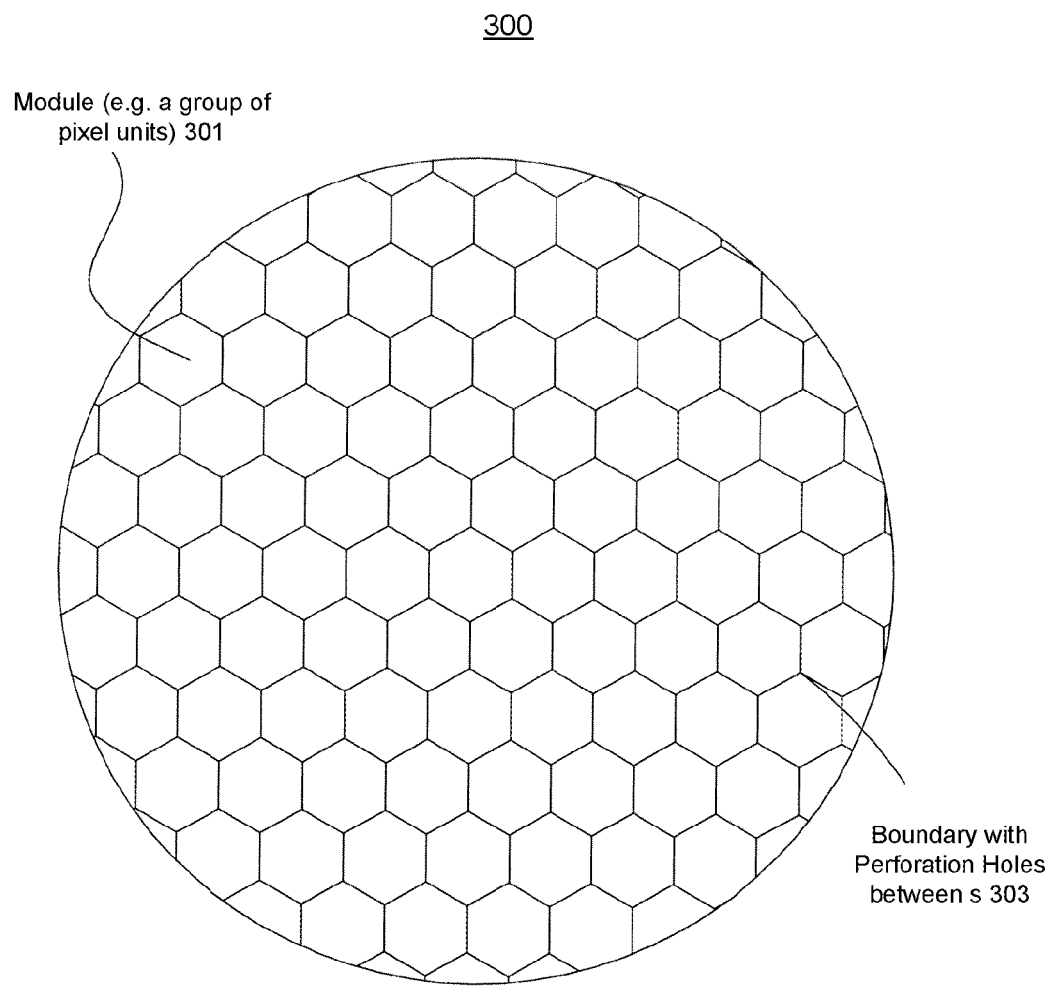
FIG. 3 is a schematic diagram illustrating an exemplary device with perforation holes according to one embodiment of the present invention.

FIG. 3 is a schematic diagram illustrating an exemplary device with perforation holes according to one embodiment of the present invention. Device 300 may be flexible in multiple dimensions to curve with at least about a curvature of average human eye ball (e.g. 25 mm in diameter). In one embodiment, device 300 may include multiple hexagonally packed modules with boundaries between adjacent modules perforated with perforation holes.

Each module, such as module 301, may include a group of pixel units in a partition of a device. The partition may be fabricated in a hexagonal shape, rectangular shape, circular shape or other applicable shapes. In one embodiment, perforation holes may allow fluid to exchange between different surfaces of device 300. Boundaries between adjacent modules, such as boundary 303 may include metal trance (or other conductive trance or conductive lines) as signal lines for the adjacent modules to directly communicate with each other. Metal trances may provide power distribution among the modules. Perforation can maintain some fluidic flow between tissues of both sides of the device (e.g. implanted within the tissues) through the perforation holes. The complete removal of integrated circuit material (e.g. silicon) except metal lines along the boundaries can increase the moldability of the device.

FIGS. 4A-4B are block diagrams illustrating cross sectional views of flexible devices in one embodiment of the present invention. Cross section 400A of FIG. 4A may indicate a flexible integrated device having multiple pixel units 417, 419, 421, 425 with layered structures, such as silicon layer 407, oxide layer 409 or biocompatible layers including polymer 401 and parylene 415. Unit 417 may include transistors 403, photo sensor 405 in silicon layer 407 and electrode 413 coupled with circuitry (e.g. including transistors 403) via aluminum 411. Perforation hole 403 may be formed across the device along a boundary between adjacent modules. For example, units 417, 419 may be grouped in one module adjacent to a separate module including units 421, 425.

Cross section 400B may indicate a cross sectional view between adjacent modules (or pixel units) of a flexible integrated device with a cutting plane across a boundary of the modules without cutting through perforation holes. Passivated metal lines or other flexible, conductive lines, such as metal wire 423, can run across the boundary (e.g. between the perforations holes) to bring electrical signals from unit to unit.

FIGS. 5A-5J are block diagrams illustrating a sequence of fabrication processes for flexible devices in one embodiment of the present invention. In one embodiment, CMOS and integration of photo sensors with electrode arrays in structure 500A of FIG. 5A may be fabricated using a standard or slightly modified CMOS technology or a CMOS image sensor (CIS) technology on silicon wafer. Preferably, the silicon wafer may comprise an SOI (Silicon On Insulator) wafer with a silicon epitaxial layer a few micrometers in thickness. A PN junction diode may be used via the modified CMOS technology as a photo sensor. Alternatively, photo sensors with optimized doping profiles may be used via the CIS technology. In certain embodiments, CMOS-compatible conducting films such as TiNi might be deposited on top of electrode layers (e.g. aluminum 511) before patterning electrodes. The electrodes may be exposed in the final pad opening step of a conventional CMOS process.

In one embodiment, structure 500A of FIG. 5A may comprise layered structures for a flexible integrated device including transistors 505, photo sensor 507, aluminum 511 for pixel unit 513 over silicon layer 503, oxide/metal layers 509, and Si substrate 501. Structure 500A may include pixel units 515, 517, 519 having similar components as in pixel unit 513. Structure 500A may have a front side (or front surface, transistor side) 537 and a back side 535 opposite to the front side 537. Front side 537 may correspond to the chip surface of a wafer or a silicon chip.

Subsequently, as shown in FIG. 5B, the front surface of a layered structure may be passivated by adhesion/barrier thin films based on, for example, SiC or DLC (Diamond-Like-Carbon) material or layers. In one embodiment, structure 500B of FIG. 5B may include barrier layer 525 as a result of the passivation. The adhesive/barrier thin films may cover already opened pad and electrode areas for a flexible integrated device, for example, at the final step of a CMOS process.

After the passivation process, pad and electrode areas may be reopened by photolithography and etching with a smaller pad size and electrode size than previously opened ones via, for example, a CMOS process. As a result, the exposed side walls surround the pads and electrodes may be protected by the adhesive/barrier layer deposited during the passivation process. The exposed side walls, if not protected or covered, may expose materials of the standard CMOS passivation layers such as PECVD (Plasma-Enhanced Chemical Vapor Deposition) silicon dioxides and silicon nitrides.

In one embodiment, a metal electrode, such as aluminum 511, may be covered by another layer of metallization (IrOx, Pt, TiN, FeOx etc.), such as electrode 521, for a better electrode-to-electrolyte interface. Afterwards, a biocompatible polymer deposition, such as biocompatible polymer (I) 523, may be applied over a barrier layer, such as barrier layer 525. The biocompatible polymer may be based on Polyimide, PDMS (Polydimethylsiloxane), Parylene, or other applicable biocompatible material. In one embodiment, the biocompatible material may be selected according to standards specified via ISO 10993 standard. After applying the biocompatible layer, in one embodiment, a first handle wafer may be bonded to the front side of the device wafer, such as handle substrate (I) 525 in FIG. 5C. Structure 500C may be ready for thinning treatment from the back side. In some embodiments, electrodes can be opened right after the biocompatible polymer layer, such as biocompatible polymer (I) 523, is deposited.

Figure 5C:
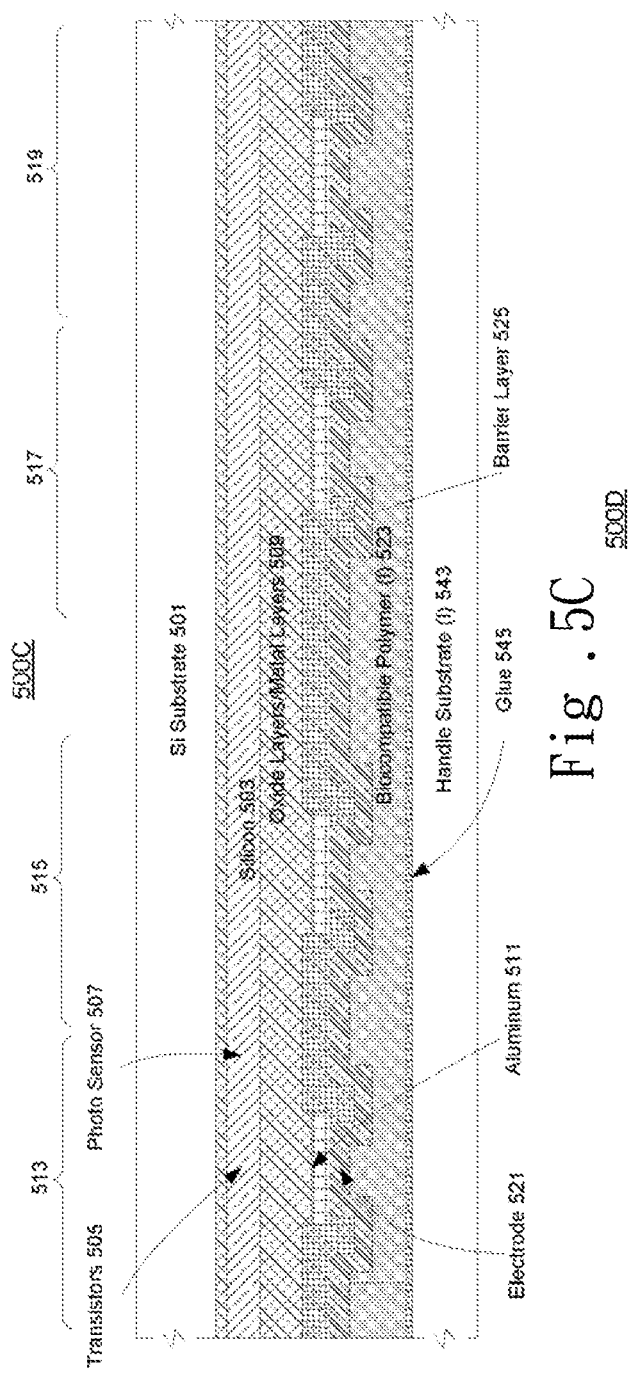
Figure 5D:
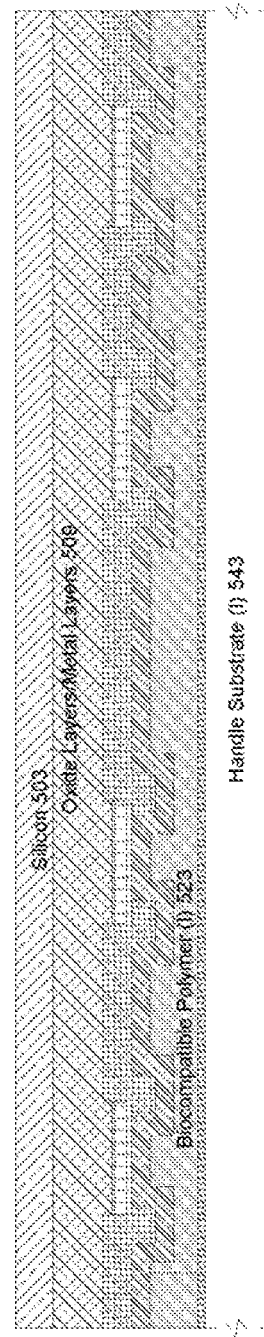
Figure 5I:
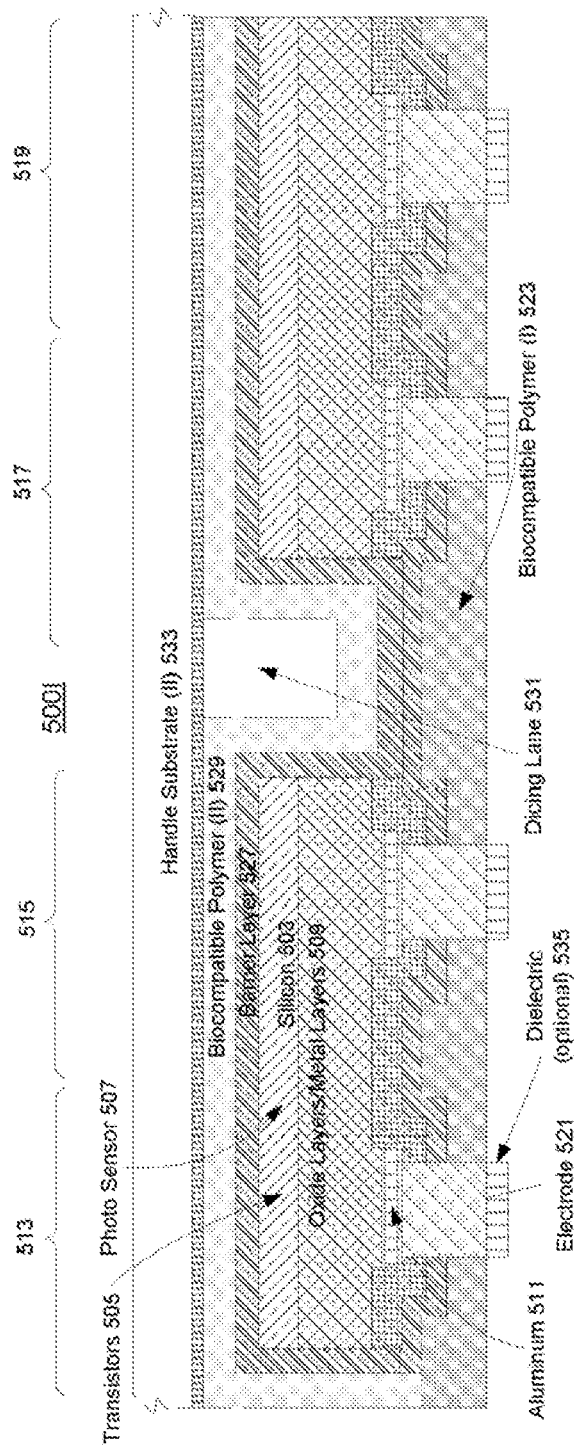
Figure 5J:
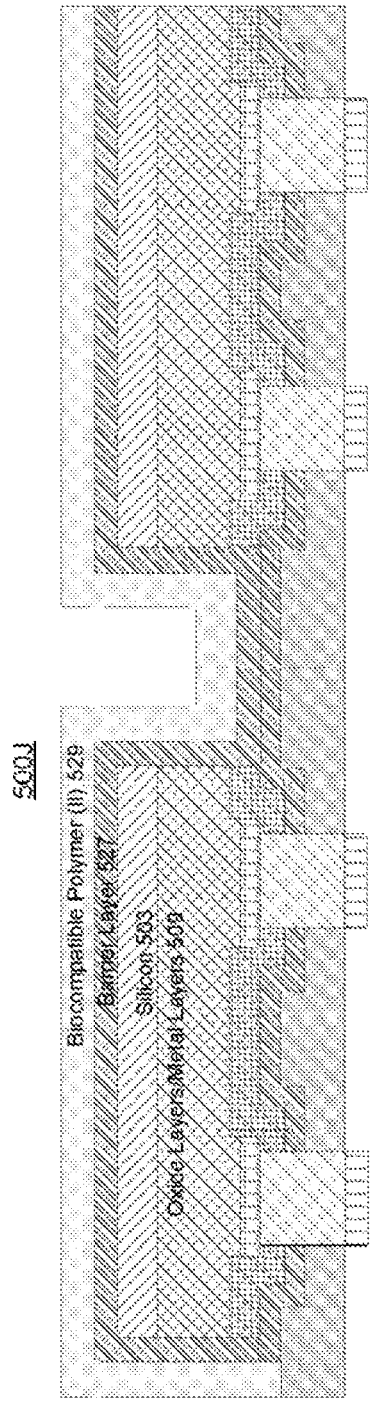

Turning now to FIG. 5D, silicon substrate of a device wafer, such as substrate 501 of FIG. 5C, can by thinned down to a proper thickness by a combination of lapping and chemical etching steps. After bonding to the carrier substrate, such as handle substrate (I) 525 of FIG. 5C, the Si wafer substrate, such as substrate 501, may then be mechanically thinned to a thickness of about 50 micrometers or other proper thickness size by a wafer lapping machine. The resulting surface may include micro-crack damages induced during the lapping process. In one embodiment, a silicon chemical etching process, such as SF6 plasma etching, dry XeF2 etching, or other applicable etching processes, may be applied to a controlled thickness to remove these damages. Alternatively, etching over a substrate using SOI may stop at the buried oxide layer as etching stop. Typically, the thickness may be controlled to be from several microns to several tens of microns such that the photo sensors can effectively absorb photons through the thickness and the substrate is still bendable to the desirable curvature. Structure 500D of FIG. 5D may include a wafer substrate which has been substantially thinned down via the thinning process.

Turning now to FIG. 5E, adhesion/barrier thin films may be deposited on a polished and/or etched surface after the thinning process. For example, barrier layer 527 may be deposited over the back side of structure 500E of FIG. 5E. Subsequently, perforation holes (or via holes) between device front and back surfaces may be patterned and opened by, for example, lithography and RIE (Reactive Ion Etching) processes or other applicable processes. For example, structure 500F of FIG. 5F may include perforation hole 531. In some embodiment, edges of a flexible device may be similarly opened as shown in open 539 of FIG. 5F.

Turning now to FIG. 5G, a polymer layer may be further etched through to a handle substrate for perforation holes. For example, structure 500G may include perforation hole 531 etched through biocompatible polymer (I) 523 to handle substrate (I) 525. Subsequently, a second biocompatible polymer layer may be deposited and patterned to open up the perforation holes. For example, biocompatible polymer (II) 529 may be deposited over the backside of structure 500G and opened for perforation hole 531. Two biocompatible layers may seal together to wrap around a device as similarly shown in seal 535 of FIG. 5G.

Subsequently, a second handle substrate may be bonded to a device on the opposite side of a first handle substrate which has already been boned to the device. The first handle substrate may be removed from the device. For example, structure 500H of FIG. 5H may include a newly bonded handle substrate (II) 533 over the back side with the first handle substrate, such as handle substrate (I) 525, removed from the front side.

After removing a handle substrate from the front surface, electrodes may be exposed by applying lithography and RIE process or other applicable processes. For example, structure 500I of FIG. 5I may include an opening through biocompatible polymer (I) 523 for electrode 521 on the front side. In one embodiment, an electrode may include an optional dielectric layer, such as dielectric 535 of FIG. 5I. Finally, a second handle wafer may be removed to complete the fabrication process of a flexible integrated device. For example, structure 500J of FIG. 5J may represent a flexible integrated device without a second handle substrate, such as handle substrate (II) 533 of FIG. 5I. FIGS. 5.1A-5.1F are block diagrams illustrating a sequence of fabrication processes for flexible devices in another embodiment of the invention.

FIGS. 6A-6D are block diagrams illustrating exemplary layered structures of flexible devices for different approaches to implant retina prosthesis. In one embodiment, a flexible integrated device for retina prosthesis can include a thin substrate to allow a portion of light to penetrate through the device (or chip) when not obstructed by metals. Thus, the monolithic chip can to be used for epi-retinal prosthesis even when the photo sensors and electrodes are fabricated on the same side (e.g. either the front side or the back side of the device).

For example, device 600A of FIG. 6A may include photo sensor 607 and electrode 615 fabricated on the front side (or transistor side) of the device. Device 600A may be implanted in an epi-retinal manner with light 623 coining from the back side of the device. In one embodiment, electrodes and photo sensors of device 600A may face the side towards retina ganglion cells 621. Device 600A may include layered structures including silicon 603 having transistors/sensors 605, oxide layers 609, guard 611 (e.g. for guard rings), aluminum 613 and optional tissue glue 617 for electrode 615, biocompatible polymer 601 wrapping the device and perforation hole 619 opened through the device.

In one embodiment, device 600A may include thin silicon substrate about less than 10 micrometers to allow more than a few percents of light coining from the back side of the device to reach the photo sensors as optical decay length of visible light may be a few microns in silicon. Thin silicon substrate may be based on fabrication processes using SOI (silicon on insulator) wafers or thinning a silicon wafer down after the MOS process.

Turning now to FIG. 6B, device 600B may include similar layered structures as in device 600A of FIG. 6A. In one embodiment, device 600B may be implanted in a sub-retinal manner with light 649 coining from the front side of the device. Electrodes and photo sensors of device 600B may face the side towards retina bipolar cells 625.

Figure 6C:
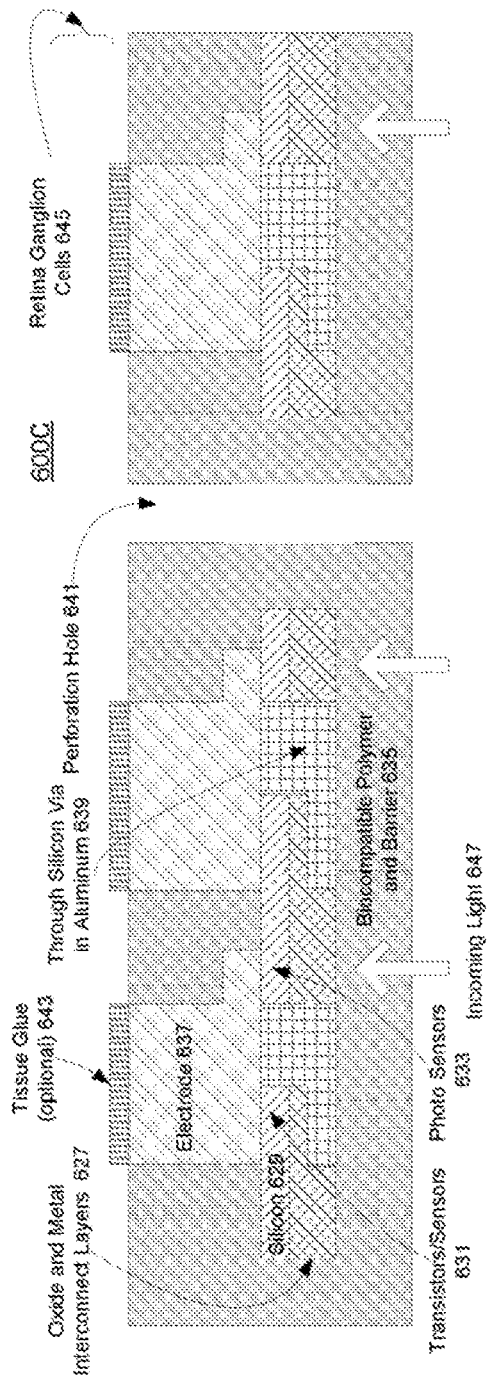

In an alternative embodiment as shown in FIG. 6C, device 600C may include photo sensor 633 on the front side and electrode 637 on the back side of the device. Advantageously, electrodes in device 600C will not block incoming light to photo sensors. In one embodiment, device 600C may be implanted in an epi retina manner with light 647 coining from the front side and electrodes facing retina ganglion cells 645 on the back side. Device 600C may include layered structures having silicon 629 with transistors/sensors 631, oxide layer 627, optional tissue glue 643 for electrode 637, biocompatible polymer 635 wrapping the device and perforation hole 641 across the front and back surfaces of the device. Electrode 637 may be coupled with processing circuitry including, for example, transistors 631, based on conducting vias, such as TSV (through silicon via) in aluminum 639.

Figure 6D:
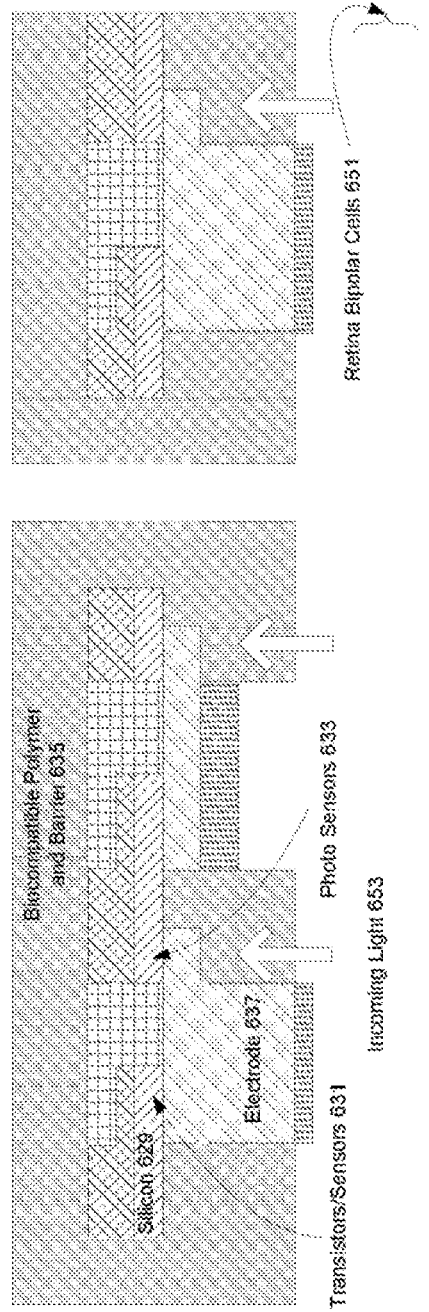

Alternatively, in FIG. 6D, device 600D may include similar layered structures as in device 600C of FIG. 6C. Device 600D may be implanted in a sub-retinal manner with light 653 coining from the back side of the device. Electrodes of device 600D may face the side towards retina bipolar cells 651.

Figure 7A:
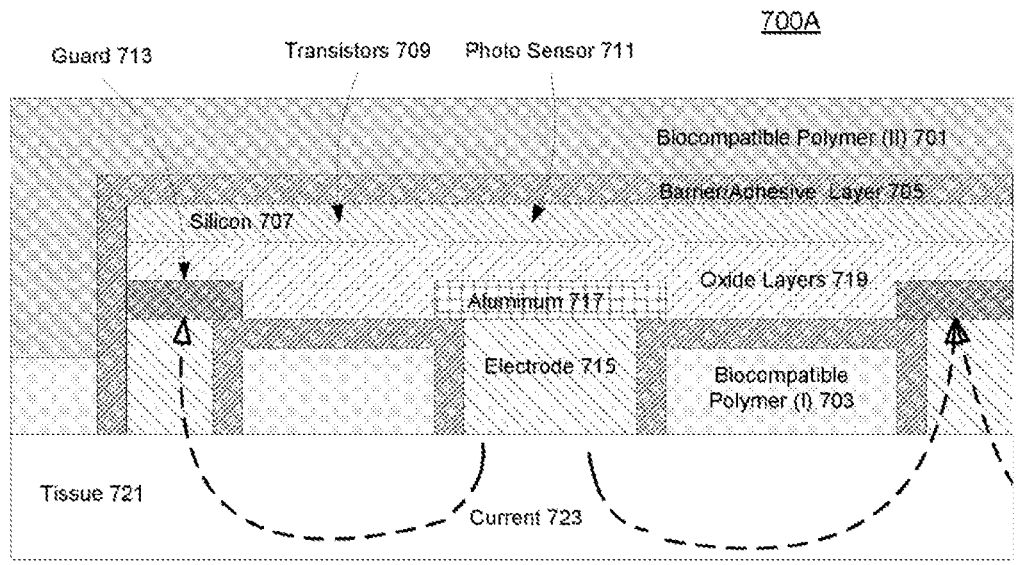
FIGS. 7A-7B are block diagrams illustrating guard rings to confine electric flows in exemplary embodiments of the present invention.
Figure 7B:
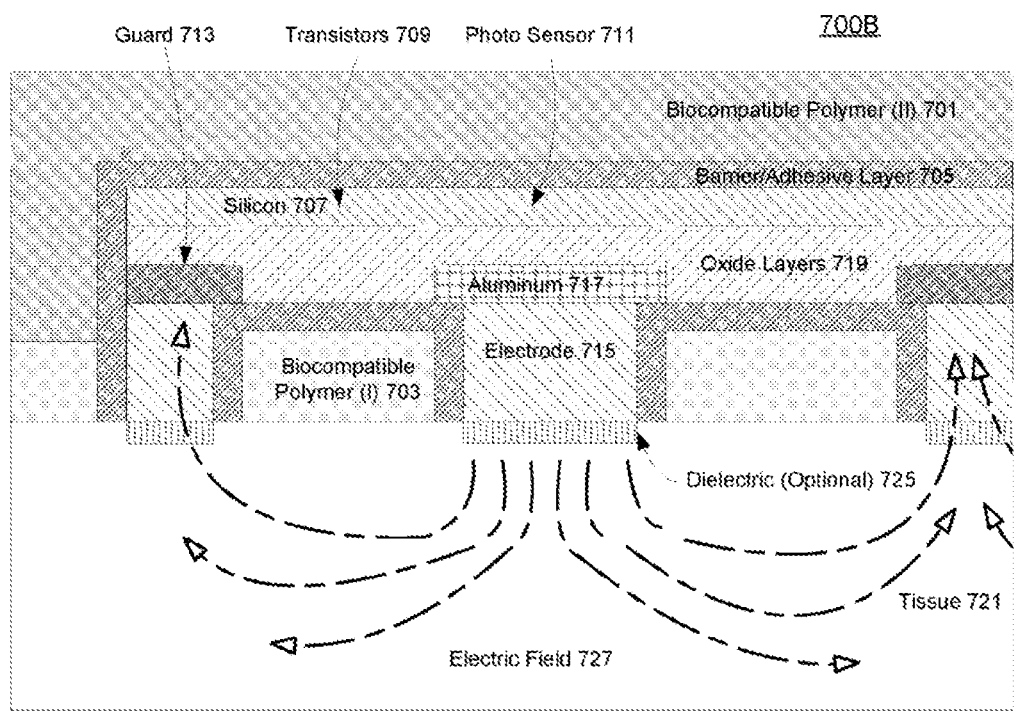

FIGS. 7A-7B are block diagrams illustrating guard rings to confine electric flows in exemplary embodiments of the present invention. Device 700A of FIG. 7A may include electrodes fitted with local return paths, or "guard ring" to confine electric flow from the electrodes. In one embodiment, device 700A may be a flexible integrated device with layered structures including silicon 707 having transistors 709 and photo sensor 711, oxide layers 719, electrode 715 over aluminum 717, and biocompatible polymer layers 701, 703 wrapping around the device over barrier/adhesive layer 705. Device 700A may be implanted within tissue 721 in a current driving mode. For example, current 723 from electrode 715 may follow the lowest impedance path. Device 700A may include guard 713 as guard ring (or local return electrode) to provide a local return path guiding current 723 from undesired target directions.

Similarly in FIG. 7B, device 700B may operate in a voltage driving mode with electric field 727 from electrode 715 confined via guard 713. Device 700B may include optional dielectric 725 for electrode 715.

Preferably, electric fields or electrical currents can be confined (or made smaller, narrower) locally close to originating electrodes through guard rings. Thus, unwanted stimulation of sensory cells other than target neurons of each electrode, such as stimulating the bipolar cells without exciting the ganglion cells, may be prevented. As a result, a flexible integrated device with guard rings may not need extra return electrodes. Electro fields from one electrode may not interfere with other electro fields from separate electrodes using guard rings. Optionally, guard rings providing limited return paths (e.g. 30 micron in length) may allow electrodes to target (or select) different layers of neuron cells (e.g. within 200-250 micron thickness of a retina).

Figure 8:
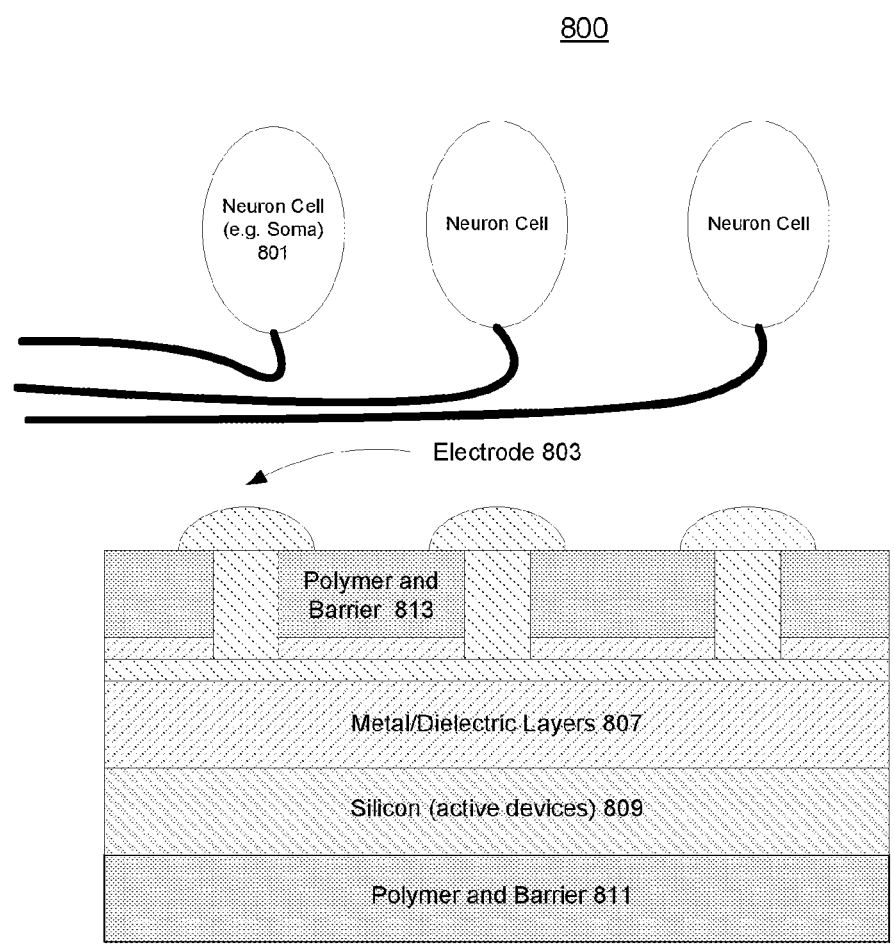
FIG. 8 is a block diagram illustrating layered structures for flexible devices with protruding electrodes in one embodiment of the present invention.

FIG. 8 is a block diagram illustrating layered structures for flexible devices with protruding electrodes in one embodiment of the present invention. For example, device 800 may comprise flexible and integrated chip with protruding electrode arrays. Device 800 may include layered structures having barrier layer 805, metal/dielectric layers 807, silicon with active components 809, and polymer 811 wrapping the device with the polymer 813. Electrode 803 may be elevated with a protruding tip in close proximity with target neuron cell 801. Preferably, when implanted, elevated stimulus electrodes can push through some of separation layers of tissues to be in closer proximity to the target locations of stimulation. Thus, the required threshold current or power to depolarize the target neurons may be reduced to enable higher number of electrodes with finer resolution.

Figure 9:
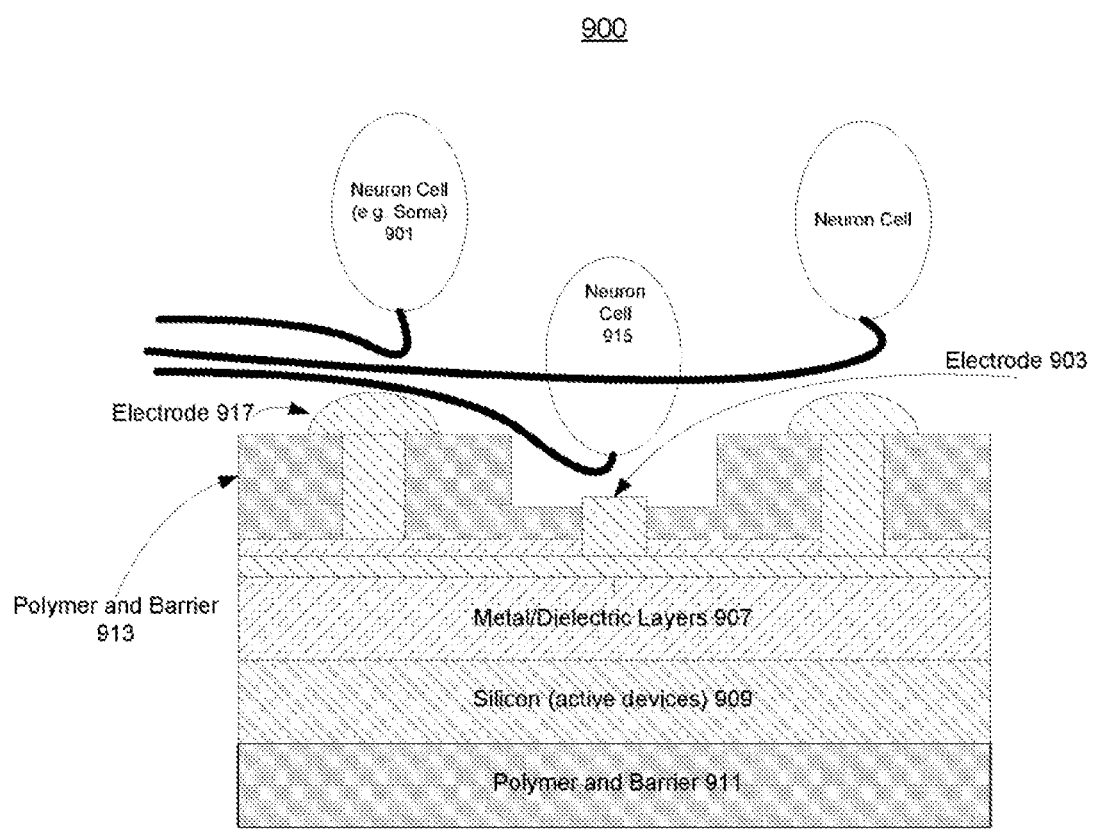
FIG. 9 is a block diagram illustrating layered structures in flexible devices with multi-level electrodes in one embodiment of the present invention.

FIG. 9 is a block diagram illustrating layered structures in flexible devices with multi-level electrodes in one embodiment of the present invention. For example, device 900 may comprise flexible and integrated chip with arrays of electrode protruding in multi-levels. Device 900 may include layered structures having barrier layer 905, metal/dielectric layers 907, silicon with active components 909, and polymer 913 wrapping the device with the polymer 911. Electrodes 917, 903 may be positioned in two different levels to separately stimulate neuron cells 901, 915.

In one embodiment, multiple-level protruding electrodes, such as electrodes 917, 903, may differentially stimulate different strata in different types of neuron cells (e.g. ON type cells, OFF type cells, or other applicable types of cells). For example, multiple-level protruding electrodes may separately target neurons ON-pathway and OFF-pathway as retina connections between bipolar cells and ganglion cells separated into two different levels of strata. The depolarizing bipolar cells may contact the On-center ganglion cells. The dendrites of these On-center ganglion cells may extend mainly into the lower part of the inner plexiform layer. The hyperpolarizing bipolar cells may contact the OFF-center ganglion cells. The dendrites of the OFF-center ganglion cells may run predominately in the upper part of the inner plexiform layer.

Figure 10A:
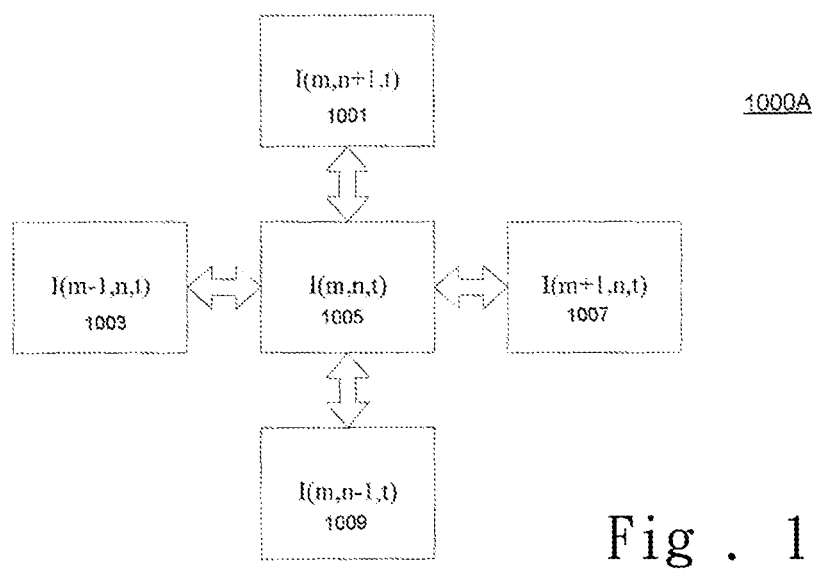
FIGS. 10A-10B are schematic diagrams illustrating exemplary signal processing circuitry in flexible devices according to one embodiment of the present invention.
Figure 10B:
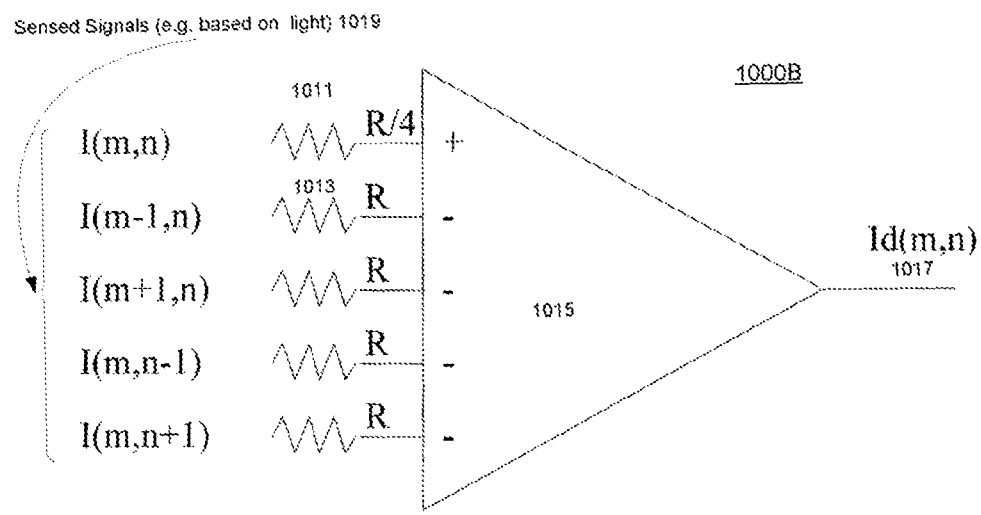

FIGS. 10A-10B are schematic diagrams illustrating exemplary signal processing circuitry in flexible devices according to one embodiment of the present invention. Device 1000A of FIG. 10A may include pixel unit 1005 coupled with neighboring pixel units 1001, 1003, 1007, 1009 in a two dimensional pixel unit array. Pixel unit 1005 may be indexed by (m, n) in the two dimensional pixel unit array to receive incoming light at time t represented by I(m, n, t). Each pixel unit may exchange information on received light with neighboring units (or other applicable pixel units).

In one embodiment, each pixel unit may include signal processing circuitry to receive inputs from neighboring pixel units. For example, referring to FIG. 10A, signals I(m, n+1,t), I(m−1, n, t), I(m, n−1, t), and I(m+1, n, t) representing light received or sensed from neighboring pixel units 1001, 1003, 1007, 1009 may be available to pixel unit 1005. The arrangement of pixel units may be based on rectangular, hexagonal (e.g. with each pixel unit having six closes neighbor pixel units), or other applicable two dimensional or multi-dimensional array.

In certain embodiments, a flexible integrated device may include signal processing circuitry capable of simulating neuron network processing mechanisms similar to the center/surround antagonism receptive field of neurons. For example, a pixel unit may generate a pixel current output (or a stimulus) proportional to the difference of the sum of center pixel light intensity and the averaged sum of surround light intensity on its neighbors to excite proper RGC spiking. In general, a pixel unit may use different weights to sum over inputs from local coupled neighboring pixel units, such as those closest neighbors, second closest neighbors, third closest neighbors, etc. to derive a processed signal derived from captured light for generating a stimulus.

For example, circuitry 1000B of FIG. 1000B may include a processing element 1015 generating a weighted output Id(m, n) 1017 from sensed signal inputs 1019 separately weighted through weigh settings 1011, 1013 (e.g. resistor components). In one embodiment, pixel unit 1005 of FIG. 10A may include circuitry 1000B for signal processing. Four of sensed signals I(m−1,n), I(m+1,n), I(m, n−1), I(m, n+1) 1019 (e.g. inputs from neighboring pixel units) may be weighted with equal weights of ¼ of sensed signal I(m, n) via resistor components, such as R 1013 and R/4 1011. In some embodiments, weights may be set (e.g. dynamically configured) to about zero (e.g. equivalent to disconnecting from corresponding neighboring pixel units) for a majority of neighboring pixel units except for those pixel units at metering locations to reduce effect of background absolute light intensity in a similar manner as multi-point metering used in digital cameras. In some embodiments, signal subtraction may be applied in processing signals exchanged from neighboring pixels units to generate stimuli based on relative intensity of incoming light instead of absolute intensity.

Figure 10C:
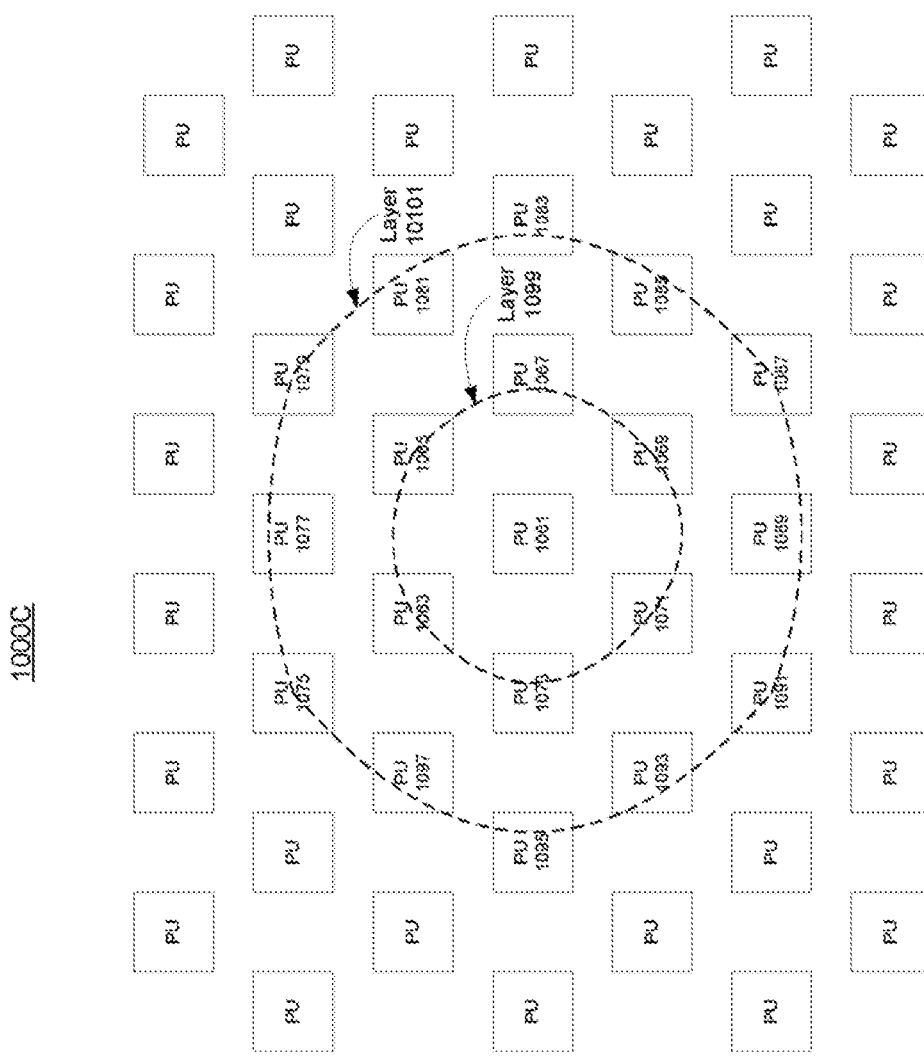
FIG. 10C is a schematic diagram illustrating an exemplary configuration of pixel units for processing signals according to one embodiment of the present invention.

FIG. 10C is a schematic diagram illustrating an exemplary configuration of pixel units for processing signals according to one embodiment of the present invention. Array 1000C may include multiple pixel units, such as PU 1061, arranged with a geometric relationship in a two (or more) dimensional manner. Each pixel unit may include components of pixel unit 107 of FIG. 1A or pixel unit 109 of FIG. 1B. PU 1061 may be positioned with layers of neighboring pixel units, such as layer 1099, layer 10101. An immediate (or closest) layer (or group) of neighboring pixel units of PU 1061 may include layer 1099 having PU 1063-PU 1073. Layer 10101 may include pixel units PU 1075-PU 1097. Distance between (immediate) neighboring pixel units, such as PU 1061 and PU 1067, may be around tens of micrometers (e.g. 30 µm). Stimuli signals generated by PU 1061 may be based on weighted sum of light signals received (e.g. inputs) via neighboring pixel units in layer 1099 and layer 10101 or more neighboring layers. For example, each layer of pixel units may be configured with a separate weight (such as using the Laplacian of Gaussian Algorithm).

Figure 10D:
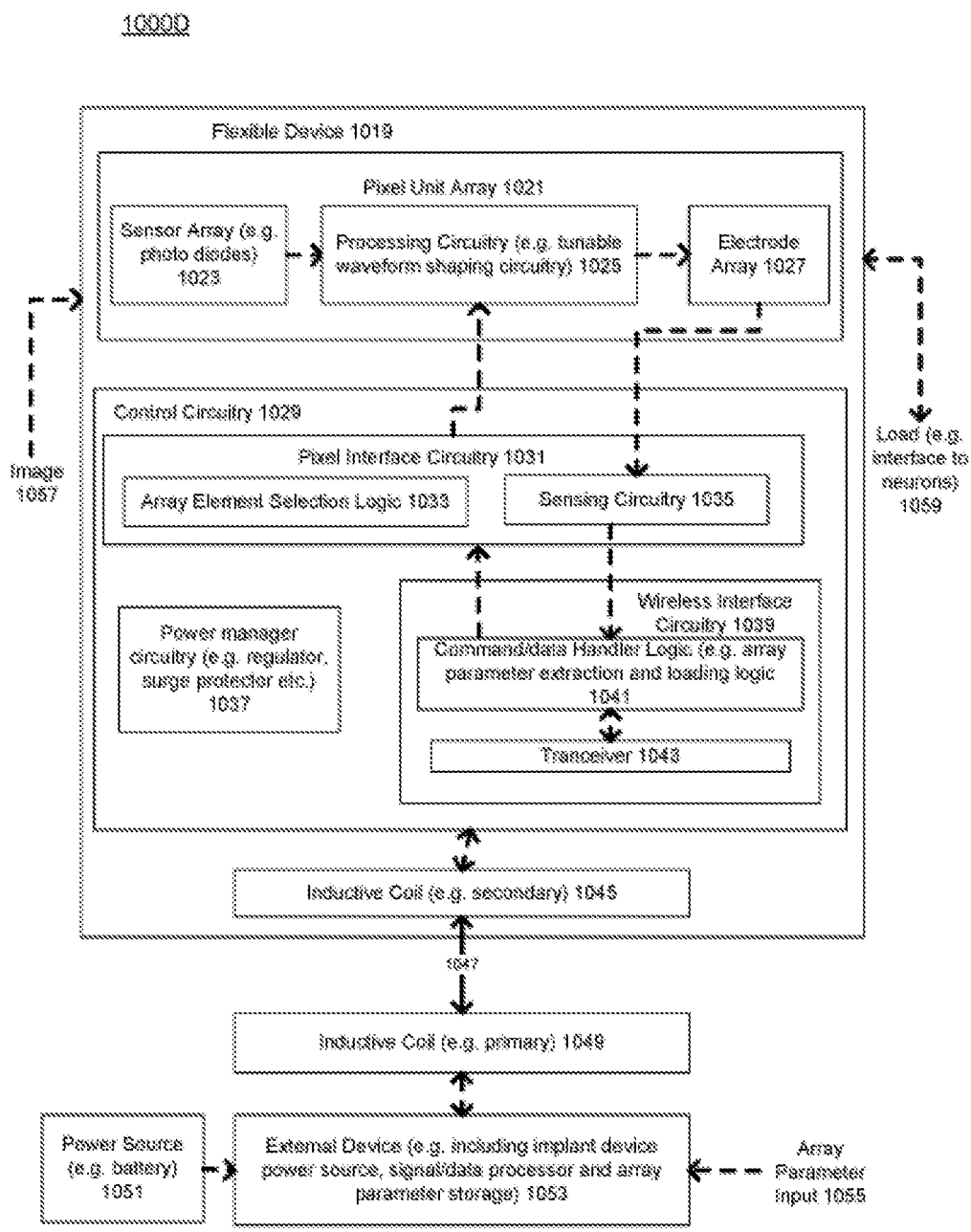
FIG. 10D is a block diagram illustrating a flexible device wirelessly configured, calibrated, and tested via an external device according to one embodiment of the present invention.

FIG. 10D is a block diagram illustrating a flexible device wirelessly configured via an external device according to one embodiment of the present invention. Flexible device 1019 may be based on, for example, device 100A of FIG. 1A or device 100B of FIG. 1B. In one embodiment, flexible device 1019 may be wirelessly coupled with external processing device 1053 via wireless path (or link) 1047. Commands/data may be transmitted over path 1047 between flexible device 1019 and external device 1053, for example, to configure, test or perform special (e.g. management, debugging, etc.) operations on flexible device 1019.

According to some embodiments, flexible device 1019 may include pixel unit array 1021, control circuitry 1029 and inductive coil 1045. External device 1053 may include inductive coil 1049 as primary coil when coupled (e.g. magnetically) with a secondary coil such as inductive coil 1045. Flexible device 1019 may draw power from implant device power source of external device 1053 via wireless path 1047 established between coils 1045, 1049. Flexible device 1019 may sense light input from image 1057 to generate stimuli driving load 1059, such as neuron cells to enable visual perception. Here for exemplifying purpose, the inductive coils are used for both transmitting power and transmitting data (for example, using ASK amplitude-shift keying or FSK frequency-shift keying), although two sets of inductive coils maybe optimized separately and used for transmitting power or transmitting data.

External device may include implant device power source, signal/data processor (e.g. microprocessors or other applicable processors), storage components (e.g. volatile or non-volatile memories) for storing parameters, for example, to configure pixel unit array 1021. External device 1053 and implant device power source may be powered via power source 1051, such as battery, solar power converter or other applicable power source. Parameters values to configure flexible device 1019 may be received from array parameter input 1055 and/or generated/computed via data processors.

In one embodiment, pixel unit array 1021 includes sensor array 1023, processing circuitry 1025 and electrode array 1027, based on, for example, pixel unit 107 or pixel unit 109 of FIGS. 1A, 1B. Sensor array 1023 may include photo diodes to detect incoming light signals. Processing circuitry 1025 may be based on mixed-signal analog and digital processing mechanism with configurable parameters according to geometric or topologic arrangements in the array of pixel units. For example, processing circuitry 1025 may include tunable waveform shaping circuitry to provide varied amounts of stimuli according to, for example, characteristics of waveform (e.g. amplitude, frequency, gain, durations, shapes etc.) or stimulus sequence generated. Processing circuitry may include different modes of operations switchable via control circuitry 1029. In some embodiments, when powered on, control circuitry 1029 may automatically reconfigure pixel unit array 1021 with a set of previously stored array parameters (e.g. locally stored or wirelessly retrieved).

Control circuitry 1029 can include pixel interface circuitry 1031, power manager 1037 and wireless interface circuitry 1039. Power manager 1037 can include low-drop out regulator LDO, multiple voltage generation circuits etc. In one embodiment, power manager 1037 may draw power wirelessly via path 1047. External commands may be received via wireless interface circuitry 1039 to access (e.g. load, retrieve, read, sense or configure etc.) pixel unit array 1021 via pixel interface circuitry 1031. For example, wireless interface circuitry 1039 may include transceiver 1043 to establish wireless link and/or communications via wireless path 1047. Transceiver 1043 may embed lightweight message protocol to enable messages communication to wirelessly exchange data/commands. The interface circuitry 1039 may also generate clock signals for internal random logic operations.

Command/data handler logic 1041 may interpret received commands and perform operations accordingly. For example, command/data handler logic 1041 may identify a mode in a mode switch command received via transceiver 1043 to cause pixel unit array 1021 to change its mode of operation via pixel interface circuitry 1031. Command/data handler logic 1041 may extract parameter values carried via received commands or instructions. The extracted parameter values may be loaded to targeted pixel units of pixel unit array 1021 according to array element selection logic 1033.

In some embodiments, testing or diagnostic commands may be received to send stimulus signals to selected pixel units for identify load or neuron characteristics to adjust array parameters in pixel unit array 1021. Command/data handler logic 1041 may deliver the stimulus instructed by the test commands to the select pixel units. Sensing circuitry 1035 may capture sensed responses via participating electrodes (e.g. in sensing mode) in electrode array 1027. Command/data handler logic 1041 may send out data carrying the sensed responses of targeted loads via transceiver 1043.

Figure 10E:
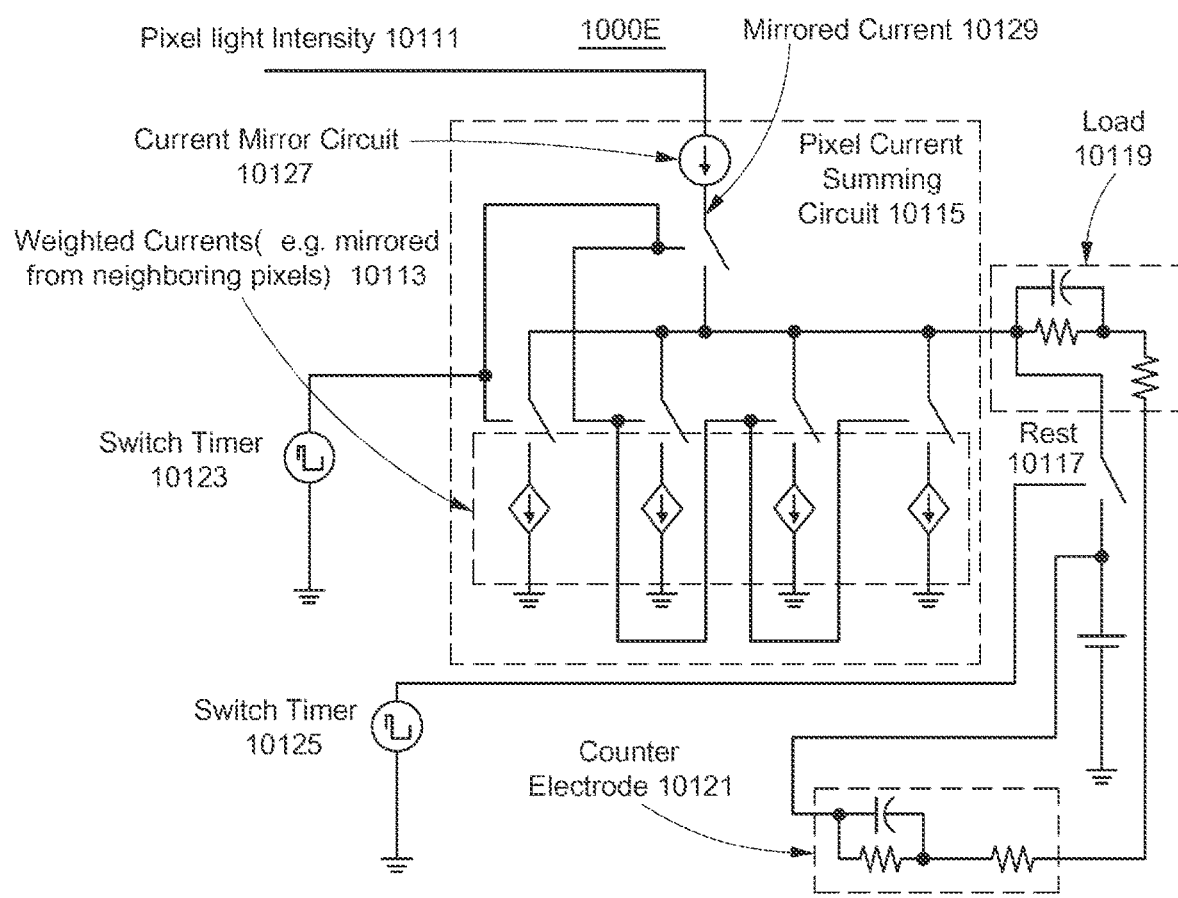
FIG. 10E is a schematic diagram illustrating another example of a signal processing circuitry in flexible devices according to one embodiment of the present invention.

FIG. 10E is a schematic diagram illustrating another example of a signal processing circuitry in flexible devices. For example, circuit 1000E may include components of processing circuitry 1025 of FIG. 10D. In one embodiment, circuit 1000E may include processing elements configured or wired (e.g. prewired, hardwired, dynamically wired) with algorithms implemented based on operations either in voltage mode or in current mode. For example, the algorithms may include Laplacian algorithm for weighted summing of signals.

In one embodiment, pixel current summing circuit 10115 may receive pixel light intensity 10111 to drive load 10119 coupled with pixel current summing circuit 10115. Pixel light intensity 10111 sensed by a pixel can be converted into mirrored current 10129 based on the amplitude of a current via, for example, current mirror circuit 10127. Pixel current summing circuit 10115 may receive weighted currents 10113 from neighboring pixels based on weighting the current amplitudes from the neighboring pixels. Mirrored current 10129 and weighted currents 10113 may be coupled to load 10119. In one embodiment, the difference of mirrored current 10129 and weighted currents 10113 can be fed into load 10119 based on the current polarity. This current may flow through counter electrode 10121 back to the internal ground. Current flows to load 10119 and reset 10117 can be controlled by switches timed by switch timers 10123, 10125.

Figure 11:
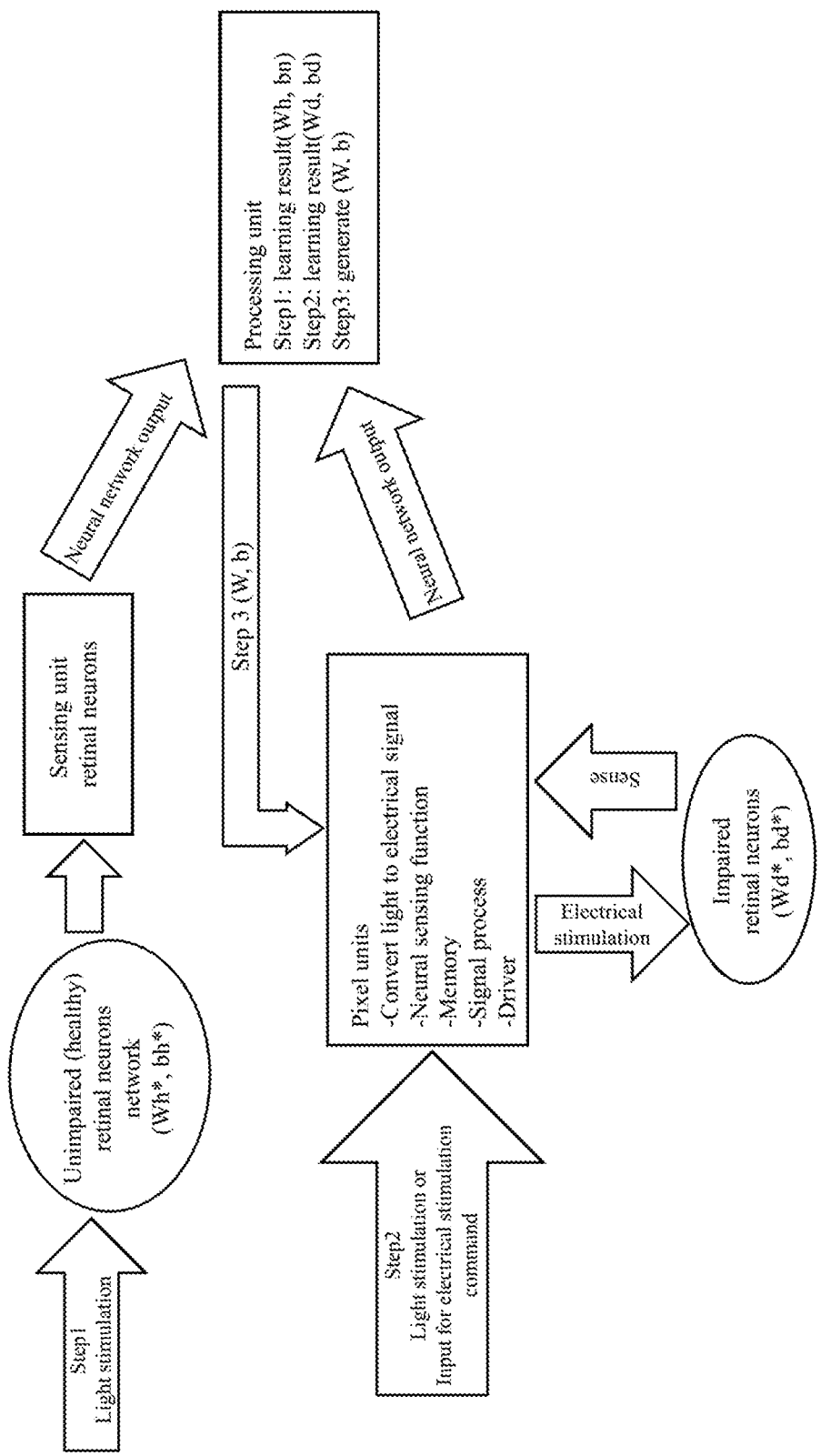
FIG. 11 is a block diagram illustrating a control method for a retina prosthesis device in exemplary embodiments of the present invention.

FIG. 11 is a block diagram illustrating a setting method for a retina prosthesis device in exemplary embodiments of the present invention. The setting method comprising the following steps. Step 1: measuring at least one first neural output from an unimpaired retinal neural network which is stimulated by a set of patterned light stimulation to extract at least one first characteristic of response for the unimpaired retinal neural network with the light stimulation. Step 2: measuring at least one second neural output from an impaired retinal neural network contacting to an implanted retina prosthesis device, which is stimulated by an electrical stimulation converted from another set of patterned light stimulation or command representing a desired electrical stimulation, to extract at least one second characteristics of response for the impaired retinal neural network in contact with the implanted retinal prosthesis device, wherein the implanted retina prosthesis device comprises an array of pixel units to receive the patterned light stimulation or the command to stimulate the impaired retinal neural network, a memory device to store configurable parameters, and a data processing unit to compute an electrical output according to the configurable parameters stored in the memory device for stimulating the impaired neural network. Step 3: computing a prosthesis setting parameters according to the first characteristics of the unimpaired retinal neural network and the second characteristics of the impaired retinal neural network so as to provide an effect of mimicking an output response of the impaired neural networks to image patterns as the unimpaired retinal neural networks.

The pixel units receive the patterned light stimulation or the command and then stimulate the impaired retinal neural network based on either the configurable parameters or the prosthesis setting parameters. The impaired retinal neural network outputs the second neural output(s) after stimulated by the electrical stimulation (the electrical output) from the pixel units.

In one embodiment, the configurable parameters and the prosthesis setting parameters are used to decide or calculate the electrical stimulation (the electrical output) based on the light stimulation (or the command). Namely, the pixel units output the electrical stimulation (the electrical output) based on the configurable parameters or the prosthesis setting parameters after received the light stimulation or the command.

The following is an example of the procedure to assign the kernel:

The average normal neural circuit response R(:) under light stimulation L(:) under a linear-nonlinear model (LN model) is a nonlinear function Nh(:) (such as a parameterized cumulative normal function, ReLu etc.) of the linear convolution of a kernel tensor function Wh(:), which representing the neural circuit, with an offset bh(:):

$$R(i, j, t) = Nh[Wh(i, j, t; k, l, tp) * L(k, l, tp) + bh(i,j)] \quad [1]$$

The Wh(:) & bh (:) can be estimated by methods such as STA (spike-triggered average) and are sparse beyond the "receptive field" in (i-k, j-l) and a "memory range" in t-tp. (ref.: Chickilnisky, Networks: Comput. Neural Syst. 12 (2001) 199-213).

The altered neural circuit response R'(:) under electrical stimulation S(:) under the LN model is a nonlinear function Nd(:) of the linear convolution of a kernel tensor function Wd(:), which representing the altered neural circuit, with an offset bd(:):

$$R'(i, j, t) = Nd[Wd(i, j, t; k, l, tp) * S(k, l, tp) + bd(i,j)] \quad [2]$$

The kernel Wd(:) can be obtained again by similar methods such as STA.

The goal is to construct the electrical stimulation S(:) as a function of light stimulation L(:), given the average normal characteristics Wh, bh & altered characteristics Wd, bd are obtained, such that R'(:) approaches R(:).

Assuming the basic non-linear characteristics of normal Nh and altered Nd are similar, then the goal of R'→R implies $$Wd(i, j, t; k, l, tp) * S(k, l, tp) + bd(i,j) \rightarrow Wh(i, j, t; k, l, tp) * L(k, l, tp) + bh(i,j)$$

Thus, $$S(k, l, t) \sim Wd^{-1}(i, j, t; k, l, tpp) * [Wh(i, j, tpp; k, l, tp) * L(k, l, tp) + (bh(i,j) - bd(i,j))] = W(i, j, t; k, l, tp) * L(k, l, tp) + b(i,j) \quad [3]$$

where $$W(i, j, t; k, l, tp) = Wd^{-1}(i, j, t; k, l, tpp) * [Wh(i, j, t; k, l, tpp);$$

$$b(i, j) = Wd^{-1}(i, j, t; k, l, tpp) * (bh(i,j) - bd(i,j)) \quad [4]$$

In summary, the appropriate electrical stimulation S(:) can be determined from the light stimulation L(:) by:

$$S(k, l, t) \sim W(i, j, t; k, l, tp) * L(k, l, tp) + b(i,j)$$

Where W(:) and b(:) (, which are derived from Wh(:), Wd(:), bh(:) & bd(:) as in [4]), can be loaded into memory (either non-volatile devices or volatile registers) of the system for real-time applications.

Figure 12A:
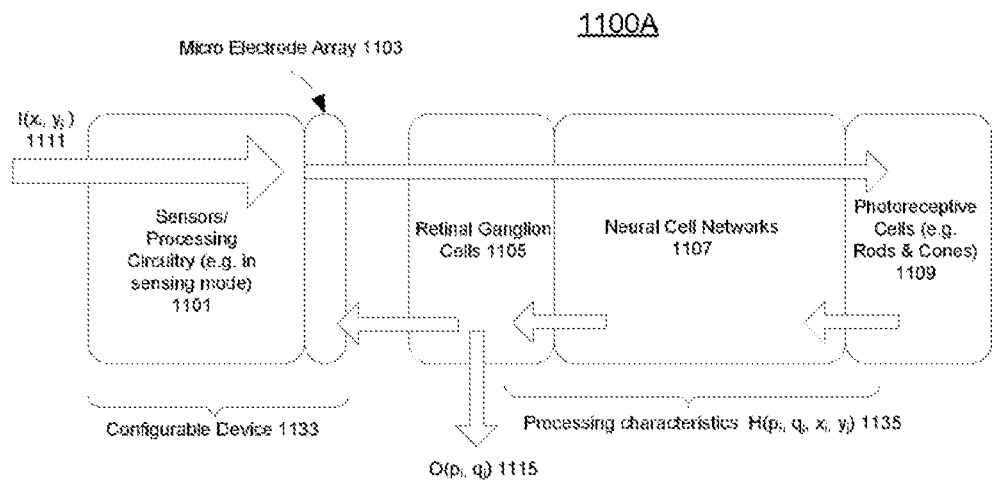
FIGS. 12A-12B are block diagrams illustrating operations of configured flexible devices in one embodiment of the present invention.
Figure 12B:
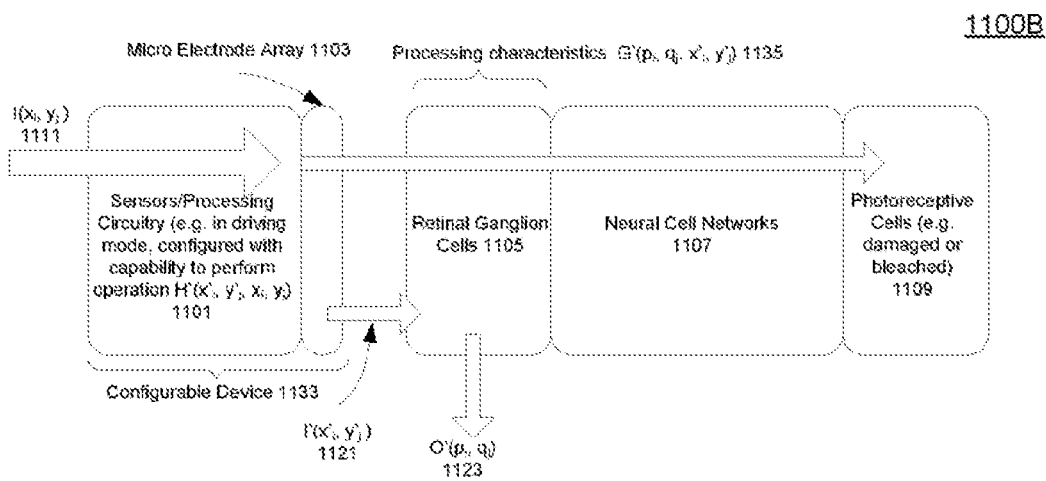

Given below is the detailed explanation regarding the above-mentioned method. FIGS. 12A-12B are block diagrams illustrating operations of configured flexible devices in one embodiment of the present invention. For example, flexible integrated device 1133 may be configurable to provide portions of functionality identified from neuron cells, such as retinal ganglion cells 1105 and/or neural cell networks 1107, to reestablish damaged or deteriorated vision perception. Neural cell networks 1107 may include neuron cells such as horizontal cells, bipolar cells, amacrine cells or other retina cells etc. Device 1133 may include processing circuitry 1101 coupled with micro electrode array 1103 capable of sending stimuli to and/or sensing responses from neuron cells.

In one embodiment, device 1133 may be configurable when operating in a calibration/programming mode. Device 1133 may operate in other modes such as a normal mode to stimulate neuron cells from incoming light to enable vision perception. In some embodiments, during a calibration/programming mode, processing circuitry 1101 may switch between a sensing mode and a driving mode to identify and configure processing characteristics (e.g. via a programmable logic array or other applicable programmable circuitry) such that proper stimuli can be generated for desired sensory output O(pi, qi) 1115 from incoming light I(xi, yi) 1111 (e.g. generated light) when a portion of the neuron cells are unable to function properly (e.g. damaged, decayed, deteriorated etc.)

For example, processing circuitry 1101 may enter a sensory mode right after sending stimulus from incoming light I(xi, yi) 1111 to normal working or relatively healthy neuron cells to produce sensory output O(pi, qi) 1115. In some embodiments, light I(xi, yi) 1111 may be generated to optically select and configure a portion (e.g. a pixel unit or a group of pixel units) of device 1133. Processing circuitry 1101 in the sensing mode may be capable of detecting responses from the neuron cells, such as retinal ganglion cells 1105. The responses may be at least one electric characteristics of the group of neuron cells, such as voltages, waveforms or other applicable signals or spikes over a period of time to represent sensory output O(pi, qi) 1115. Processing circuitry 1101 may store information including relationship between incoming light and the corresponding responses detected. The information may represent inherent processing characteristics H(pi, qj, xi, yi) 1135 in neuron cells, for example, based on the relationship indicated by the expression O=H*I.

Subsequently, as shown in FIG. 12B, processing circuitry 1101 may be configured to perform operations to make up for lost or altered visual information processing capabilities of neuron cells. For example, photoreceptive cells 1109 may be damaged or bleached to block neural cell networks 1107 from processing sensed light signals. As a result, visual perception may be based on processing characteristics G'(pi, qj, x'i, y'j) 1135 of retinal ganglion cells 1105.

In one embodiment, processing circuitry 1101 may be configured (e.g. automatically or manually) to perform operation (or transform operation) H'(x'i, y'j, xi, yj). For example, stimuli to retina ganglion cells 1105 may be generated in the configured processing circuitry 1101 according to effective light input I'=H'*I to allow perceived output O'(pi, qj) 1123 (e.g. corresponding to a result of operations G'*I') to be close to O(pi,qj) 1115. In one embodiment, H'(x'i, y'j, xi, yj) may be programmed based on inherent processing characteristics H(pi, qj, xi, yj). Processing circuitry 1101 may operate in a driving mode to configure the processing capabilities. Device 1133 may operate in a normal mode of operation, or in a calibration mode of operation for further fine tuning or adjustment of the configured processing capabilities.

In one embodiment, processing circuitry may incorporate electrical sensing circuitry to enable measurement of retina neuron response kinetics during a calibration mode, for example, when device 1133 is implanted in an epi-retina manner. With the ability to switch the device (or chip) to electrical sensing right after electrical stimulation, the ON cells and OFF cells can be identified through the response time, and this information can be used to formulate the specific electrical stimulus from the nearby electrode when local light information is sensed by photo sensors on the device.

Figure 13:
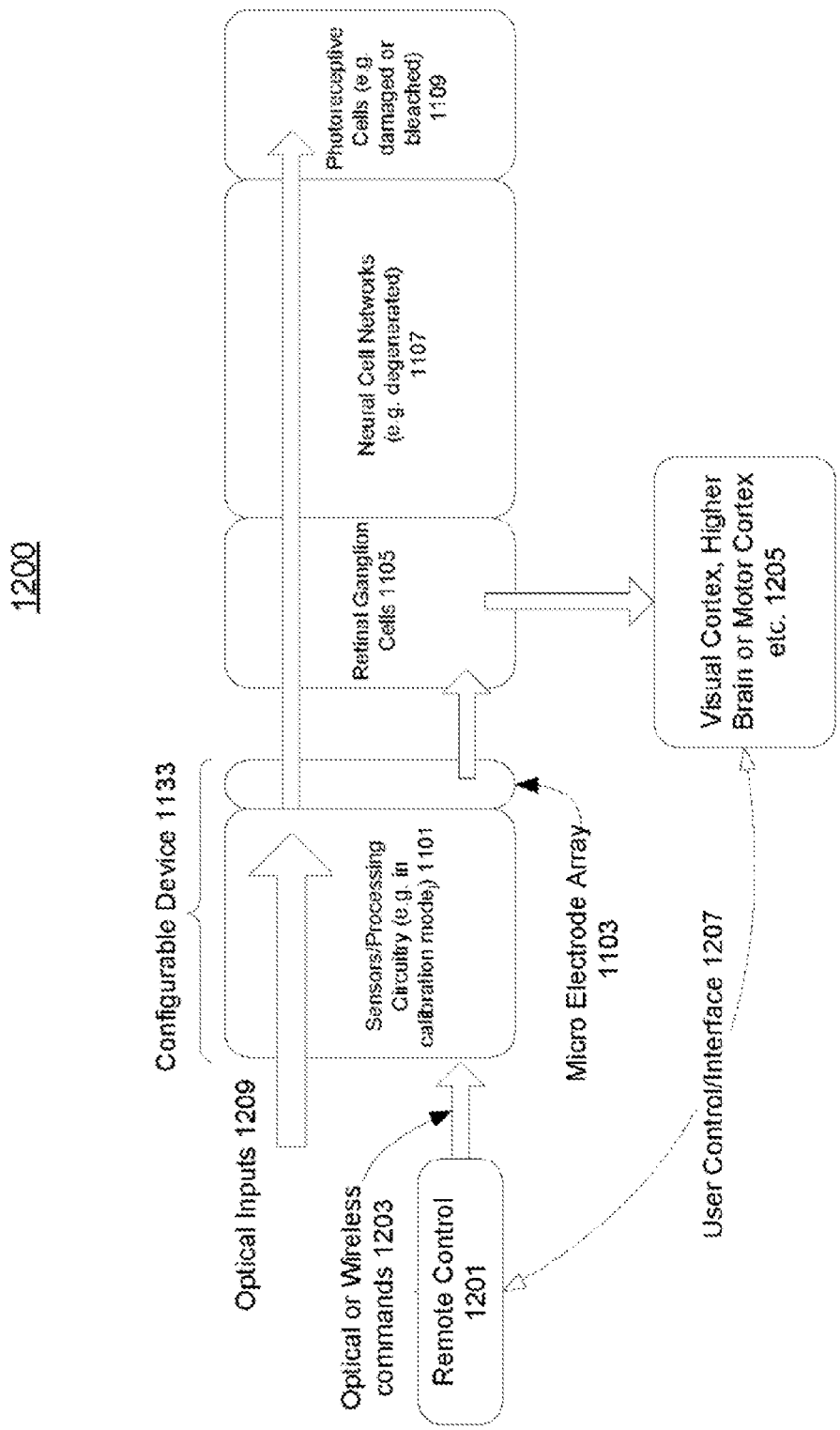
FIG. 13 is a block diagram illustrating a system to configure flexible devices in one embodiment of the present invention.

FIG. 13 is a block diagram illustrating a system to configure flexible devices in one embodiment of the present invention. System 1200 may include configurable retinal prosthesis device 1133 with on-chip processing circuitry 1101 optically or wirelessly coupled with external or remote control device 1201 to provide a control or feedback path for tuning/adjusting configurable device 1133. In one embodiment, processing circuit 1101 and electrode array 1103 may include electrical parameters or settings which can be self configured or externally updated (e.g. via external commands). For example, characteristics of system 1200, such as light sensitivity, stimulus intensity, or other applicable parameters may be changed to achieve desired visual perception via these settings. Alternatively or optionally, configurable device 1133 may include a configuration for generating stimuli from incoming light captured. In one embodiment, a patient may operate remote control 1201 via user control 1207 based on perceived visions in visual cortex 1205.

In some embodiments, external commands 1203 may be optical commands included in optical inputs 1209 which may comprise predetermined visual patterns. Alternatively, external commands 1203 may be wirelessly transmitted (e.g. based EM signals) to device 1133 via wireless transceiver. Device 1133 may include certain light sensing pixels together with special decoding circuit on chip to detect special light pulse pattern from optical input 1203 to enter the chip into calibration mode for tuning/adjustment. Alternatively, the external commands may wirelessly cause device 1133 to enter a calibration mode or other modes of operation.

In one embodiment, each pixel or regions of pixels of device 1133 may be separately accessed optically or wirelessly through light projection (e.g. into the eye on the implanted region). The pixel or regions can be electrically accessed on chip to tune electrical stimulus parameters to achieve targeted effects of visual sensation. In one embodiment, test patterns, e.g. via optical input 1209, can be projected onto the implanted retina or directly viewed by implanted patients. The targeted visual effects may be described to the patients for conducting manual tuning on parameters of implanted retina prosthesis chips using the external optical input device to allow better approximation of the targeted visual effects.

FIG. 14 is a flow diagram illustrating a method to configure flexible devices in one embodiment described herein. Exemplary process 1300 may be performed by a processing circuitry that may comprise hardware (circuitry, dedicated logic, etc.), software (such as machine code executed in a machine or processing device), or a combination of both. For example, process 1300 may be performed by some components of system 1200 of FIG. 13.

In one embodiment, the processing logic of process 1300 may detect light patterns (e.g. predetermined or dynamically generated) from received light via photo sensors at block 1301. The processing logic of process 1300 may decode the captured light to extract the light patterns optically encoded in the light. On detecting the light patterns, the processing logic of process 1300 may cause a device to enter a calibration mode for configuration. The device may comprise an array of pixel units to receive light to enable perception of a vision from the light. The pixel units are configurable via electrical parameters.

At block 1303, in one embodiment, the processing logic of process 1300 may receive light patterns to select one or more of an array of pixel units in a flexible integrated device. The light patterns may be associated with known effects of visual sensation. For example, a patient implanted with the device may be aware of which visual perception to be expected, such as the shape of the image of light, the relative intensity of the image of light or other visual effects. At block 1305, the processing logic of process 1300 may generate stimuli from selected pixel units to stimulate neuron cells to cause actual effect of visual sensation similar to a normal person should experience with the light patterns received. In some embodiments, the light patterns may include selection light patterns to identify which pixel units should be selected.

Subsequently, at block 1307, in one embodiment, the processing logic of process 1300 may receive external commands to update electrical parameters of a flexible integrated device. The external commands may be optically or wirelessly received. The processing logic of process 1300 may update the electrical parameters to cause adjustment of actual effects of visual sensation from the light patterns (or other applicable incoming light) received via the selected pixel units updated with the electrical parameters. The captured light (e.g. the light patterns) may be associated with known visual effects. As a result of the update, the actual effect of visual sensation may be adjusted to match the known effects of visual sensation to proper configure the device. In some embodiments, light patterns may be separately generated for pixel selection and for electrical or circuitry updates on the selected pixels.

Figure 15:
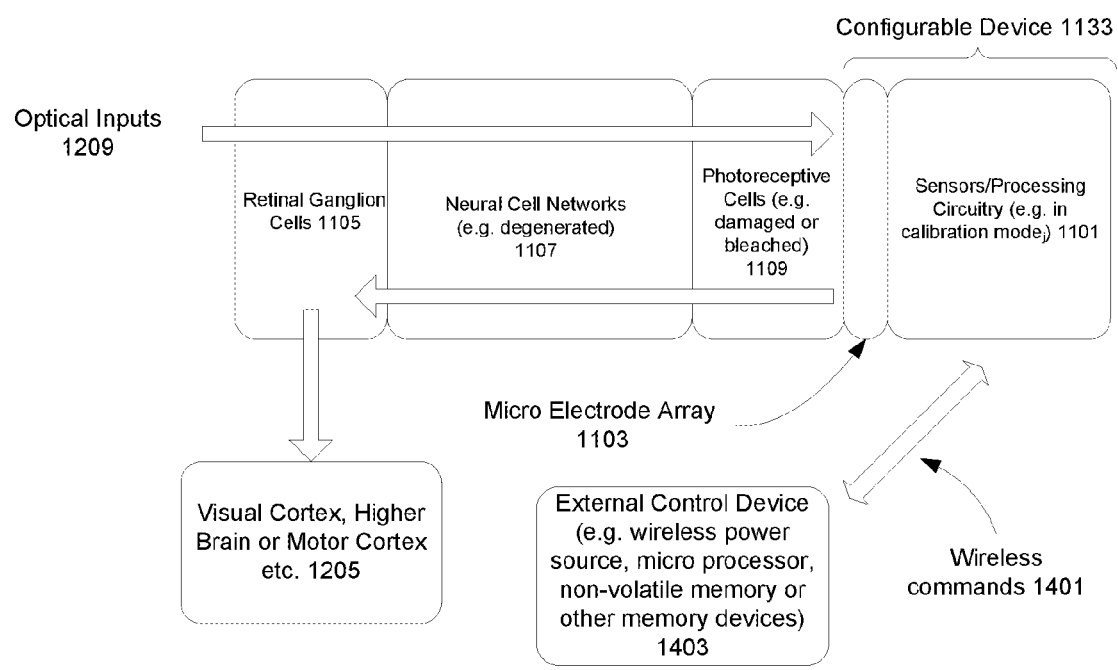
FIG. 15 is a block diagram illustrating a system to configure flexible devices in another embodiment of the present invention.

FIG. 15 is a block diagram illustrating a system to configure flexible devices in another embodiment of the present invention. System 1400 may be based on configurable device 1133 including circuitry 1101 and electrode array 1103. In one embodiment, configurable device 1133 can provide configurability through switchable digital logics to vary its output stimulating waveform to retinal neurons. Pixel calibration data can be stored in external control device 1403, which may include wireless power source, microprocessor, memory devices and external data interface. External control device 1403 may send wireless commands 1403, for example, to configure configurable device 1133.

In one embodiment, pixel calibration data can be periodically updated from external control device 1403 to configurable device 1133, for example, based on visual examination on a user. These data may be uploaded wirelessly to registers of implanted configurable device 1133 at its "power on" (e.g. when the device is switched on) so the implanted configurable device 1133 doesn't require the integration of a non-volatile memory or other memory devices associated with a processor logic (such as a microprocessor).

Figure 16:
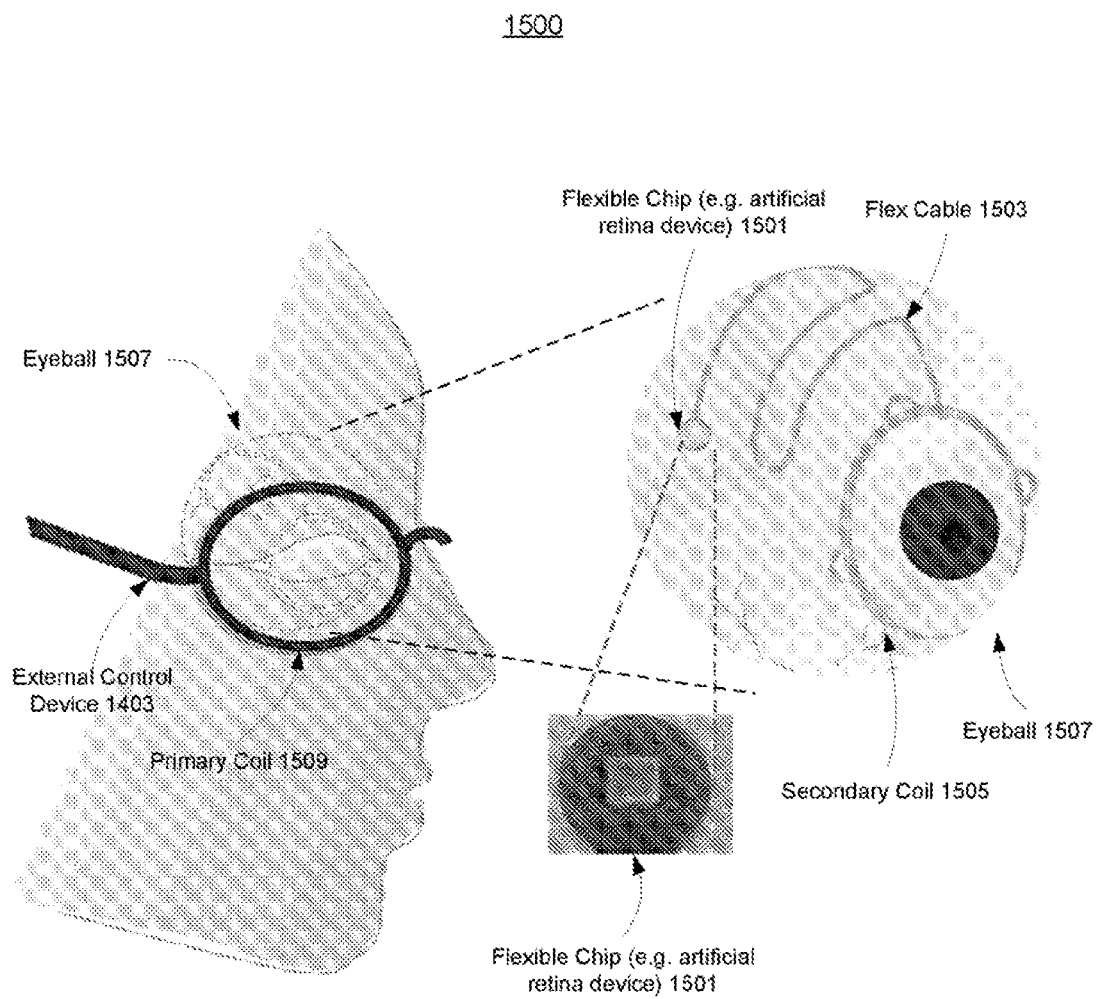
FIG. 16 is a perspective diagram illustrating an exemplary configuration of a flexible retina device coupled with a control device.

FIG. 16 is a perspective diagram illustrating an exemplary configuration of a flexible retina device coupled with a control device. Configuration 1500 may be based on flexible chip 1501 including configurable device 1133. External control device 1403 and primary coil 1509 may be embedded in a wearable fixture, such as a pair of eyeglass. Flexible chip 1501 coupled with secondary coil 1505 via flex cable 1503 may be implanted in eyeball 1507. A wireless link may be established between external control device 1403 and flexible chip 1501 via primary coil 1509 and secondary coil 1505, for example, to transport wireless commands and/or power from external control device 1403 to circuitry in flexible chip 1501.

FIG. 17 is a flow diagram illustrating another method to configure flexible devices in one embodiment described herein. Exemplary process 1600 may be performed by a processing circuitry that may comprise hardware (circuitry, dedicated logic, etc.), software (such as machine code executed in a machine or processing device), or a combination of both. For example, process 1600 may be performed by some components of system 1000D of FIG. 10D or system 1400 of FIG. 15.

In one embodiment, the processing logic of process 1600 may detect diagnostic (or test) commands from waveforms received at an interface of a device at block 1601. The interface may include a wireless transceiver, such as transceiver 1043 of FIG. 10D. The device may comprise an array of pixel units to receive light to stimulate neuron cells to cause an effect of visual sensation from the light. The pixel units can have configurable parameters for the stimulation to the neuron cells. In certain embodiments, the interface may be based on wireless signals (e.g. waveforms) which may carry power to wirelessly power the device. The diagnostic commands can be embedded within the wireless signals.

For example, the pixel units can deliver stimuli from an optical input to the neuron cells. The stimuli can cause known visual sensation via a network of neuron cells. The adjustable components may be configured to allow the pixel units to generate updated stimuli from the optical input to cause the known visual sensation without requiring the presence or the working of the network of neuron cells.

At block 1603, the processing logic of process 1600 may send data related to electric characteristics of the neuron cells via the wireless interface according to the diagnostic commands received. For example, the processing logic of process 1600 can detect mode change commands from the wireless signals at the interface. The mode change commands may be processed, e.g. via wireless interface circuitry 1039 of FIG. 10D, to cause the device to enter a particular mode, such as a neuron identification mode, a test mode, a calibration mode or other applicable mode (e.g. from an operating more or regular usage mode). In one embodiment, the diagnostic commands may be received in the neuron identification mode to collect multiple samples (e.g. over sampling) of the electrical characteristics (e.g. one sample for each sample of sensed data). The electrical characteristics may be sensed via electrodes (e.g. electrode array 1027 of FIG. 10D) in a sensing mode for each sample data collected.

The processing logic of process 1600 can send multiple samples of data carrying measurements (e.g. via sensing) of the electrical characteristics of the neuron cells to an external processing device, such as device 1053 of FIG. 10D. Different types of the neuron cells or effective electric load may be determined based on the electrical characteristics. Sophisticated data processing operations may be performed on the data carrying sampled electrical characteristics (e.g. in multiple samples) to derive (e.g. removing background noises included in the sensed electrical characteristics). At block 1605, the processing logic of process 1600 may detect configuration commands received at the interface after sending data (e.g. in multiple samples) carrying electrical characteristics of the neuron cells to the external processing device.

At block 1607, the processing logic of process 1600 may update the configurable parameters according to the configuration commands detected. The processing logic of process 1600 can generate the stimulation according to the updated configurable parameters to improve the effect of visual sensation from the light at block 1609.

In one embodiment, an implantable device, such as device 1501 of FIG. 16 or device 1019 of FIG. 10D, can interface with retina cells for retina prosthesis. The device can comprise an array of pixel units, such as pixel unit array 1021 of FIG. 10D, capable of receiving light and stimulating the retina cells to enable perception of received light. Each pixel unit can include an electrode, an associated photo sensor and a processing circuitry. The photo sensor can receive incoming light. The electrode can stimulate targeted neuron cells. The processing circuitry may generate a stimulus from the received light for the electrode to deliver to the targeted neuron cells. The pixel units may include adjustable components to accommodate different amounts of stimulation to the retina cells.

A control circuitry of the device, such as control circuit 1029 of FIG. 10D, may be capable of configuring the adjustable components for the pixel units. In one embodiment, the control circuit can include a wireless interface circuitry, such as wireless interface circuitry 1039 of FIG. 10D, and a pixel interface circuitry, such as pixel interface circuitry 1031 of FIG. 10D. The wireless interface circuitry can allow external communications to configure, calibrate, or test the pixel units or device. The pixel interface circuitry can allow selective access to the pixel units, for example, according to commands received from external communication to an external processing device, such as device 1053 of FIG. 10D.

The processing circuitry of the array of pixel units can perform processing functions according to the adjustable components updated by the parameter values for the configuration. For example, photo sensors of the array of pixel units may be associated with electrical parameters determined by the adjustable components. Sensitivity of the photo sensors to the change of incoming light may depend on the associated electrical parameters. In one embodiment, the light (or incoming light) may include a background light. The parameter values may be configured depending on the background brightness to dynamically change the sensitivity of the photo sensors to reduce effect of the absolute background light intensity of the light.

In one embodiment, the pixel unit may be coupled with neighboring pixel units in the array. An intensity signal from the photo sensor may indicate received light. The pixel unit may receive intensity signals from the neighboring pixel units to perform signal processing operations on the intensity signals directly received and/or indirectly received from the neighboring pixel units. For example, a weighed combination of the intensity signals may be performed to reduce the effect of absolute background light intensity. The weight combination may depend on weights configured according to the adjustable components.

Each pixel unit of an array of pixel units may be arranged with one or more layers of neighboring pixel units in the array. Each layer of neighboring pixel units may correspond to those pixel units located within a predefined range of distances to the pixel unit. A neighboring pixel unit may not belong to separate layers of neighboring pixel units (i.e. non overlapping). The neighboring pixel units from which the intensity signals are received for the pixel unit may include multiple layers of neighboring pixel units. In other words, multiple layers of neighboring pixel units may be considered in deriving the stimulation signal of a pixel unit. Each layer of pixel units may be defined according to similar inter unit distance to this pixel unit.

In one embodiment the adjustable components of the pixel units may be configured to adjust the amount of stimulation to the retina cells without requiring a processor (e.g. processing logic capable of executing instructions stored in a memory or storage components) in the device. In one embodiment, the adjustable components may be coupled with one or more registers to store the parameter values for the configuration. Alternatively or optionally, the adjustable components may include one or more variable resistors whose resistances updated by the parameter values as configured.

In some embodiments, configuration of the device can be based on parameter values wirelessly received via external commands received, for example, over a wireless communication. For example, a wireless interface circuitry of the device can be coupled with an induction coil to establish wireless link, such as link 1047 of FIG. 10D. The wireless link may be established based on magnetic induction mechanism, RF mechanism, or other applicable low power wireless communication mechanisms. Data signals may be embedded within the wireless link to carry external commands to the device. The wireless link may be capable of carrying power from external source, such as device 1053 of FIG. 10D, to drive the device.

In one embodiment, the device may include a decoding logic to extract the external commands, such as configuration commands, from the data signals. The control logic of the device may include detection logic (e.g. in transceiver 1043 of FIG. 10D) to detect arrival of the external commands wirelessly received to allow continuous tuning of the adjustable components as the light changes.

The external commands (e.g. configuration commands) received can identify a portion of the array of pixel units to configure the adjustable components with the parameter values for the identified portion of the array of pixel units (i.e. without affecting other portions of the array of pixel units). In certain embodiment, an array of pixel units can be partitioned into a plurality of two dimensional zones. The identified portion of the array of pixel units may correspond one of the zones to configure the parameter values for each pixel unit of the identified zone.

In one embodiment, the pixel units may be selectively accessed (e.g. via addresses received from external commands) to load, retrieve or identify electrical parameters of one or more of the pixel units. For example, request commands may be received at the device via a wireless communication from an external device to trigger or cause selective access of the pixel units. The request commands may select (or address) one or more pixel units to transmit electrical parameters of the selected pixel units to an external processing device. Subsequently, parameter values determined based on these electrical parameters may be received at the device to configure the selected pixel units.

The array of pixel units may include one or more modes of operations, such as a diagnostic mode (e.g. for detecting whether the device has any defect), operating (or usage) mode, calibration mode, assisted usage mode, neuron identification mode, or other applicable modes. The array of pixel units may switch from one mode to another mode (e.g. from a first mode to a second mode) based on external commands received over a wireless communication.

In one embodiment, a device, such as device 1403 of FIG. 16, to configure an array of pixel units of an implantable device can include a driver logic to send commands wirelessly to the implantable device, a memory to store executable instructions, a sensor components (e.g. array of light sensors or other applicable sensors) to detect environment status (e.g. background light intensity) for the implantable device and a processing logic to execute the instructions for configuring the implantable device. In one embodiment, the implantable device may interface with retina cells to cause visual sensation via light received via the pixel units.

The driver logic may be coupled with a primary coil capable of remotely coupling with the implantable device, for example, via a secondary coil of the implantable device. A wireless link may be established between the primary and secondary coils to carry commands to configure the pixel units in the implantable device. For example, the commands may include configuration settings stored in the memory of the device for configuring the pixel units. In some embodiments, the wireless link may carry power from the primary coil to the secondary coil to power the implantable device wirelessly. The configuration commands may be embedded in the wireless link carrying the power.

In one embodiment, the processing logic may determine parameter values for configuring the pixel units based on the environmental status detected and the settings stored in the memory. The processing logic may compose and send configuration commands including the parameter settings determined to the implantable device via the driver logic.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A setting method for a retina prosthesis device, the method comprising:
    measuring at least one first neural output from an unimpaired retinal neural network which is stimulated by a set of patterned light stimulation to extract at least one first characteristic of response for the unimpaired retinal neural network with the patterned light stimulation;
    measuring at least one second neural output from an impaired retinal neural network contacting to an implanted retina prosthesis device, which is stimulated by an electrical stimulation converted from another set of patterned light stimulation or command representing a desired electrical stimulation, to extract at least one second characteristics of response for the impaired retinal neural network in contact with the implanted retinal prosthesis device,
    wherein the implanted retina prosthesis device comprises:
    an array of pixel units to receive the light stimulation or the command to stimulate the impaired retinal neural network,
    a memory device to store configurable parameters, and
    a data processing unit to compute an electrical output according to the configurable parameters stored in the memory device for stimulating the impaired neural network;
    computing prosthesis setting parameters according to the first characteristics of the unimpaired retinal neural network and the second characteristics of the impaired retinal neural network, and stimulating the impaired retinal neural network based on the prosthesis setting parameters by the array of pixel units of the implanted retina prosthesis device, so as to provide an effect of mimicking an output response of the impaired neural networks to image patterns as the unimpaired retinal neural networks.

\* \* \* \* \*